United States Patent
Hansen et al.

(10) Patent No.: US 8,058,078 B2
(45) Date of Patent: Nov. 15, 2011

(54) DEVICE FOR AUTOMATICALLY ADJUSTING THE BACTERIAL INOCULUM LEVEL OF A SAMPLE

(75) Inventors: Timothy Hansen, Spring Grove, PA (US); Mark Anthony Messina, Manchester, NH (US); John Thuin Page, White Hall, MD (US); Thomas Paul Borgoyn, Eldersburg, MD (US); Ammon David Lentz, York, PA (US); Robert Michael Novak, Abingdon, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/016,040

(22) Filed: Jan. 28, 2011

(65) Prior Publication Data
US 2011/0123975 A1     May 26, 2011

Related U.S. Application Data

(62) Division of application No. 11/691,662, filed on Mar. 27, 2007, now Pat. No. 7,901,624.

(60) Provisional application No. 60/847,244, filed on Sep. 26, 2006.

(51) Int. Cl.
G01N 15/06 (2006.01)
G01N 33/00 (2006.01)
G01N 33/48 (2006.01)

(52) U.S. Cl. ...... 436/174; 422/68.1; 422/63; 422/82.05; 436/43; 436/179; 436/180

(58) Field of Classification Search ............... 422/68.1, 422/63, 82.05; 436/43, 174, 179, 180
See application file for complete search history.

(56) References Cited

U.S. PATENT DOCUMENTS

| 3,609,040 A | 9/1971 | Kuzel et al. |
| 3,912,393 A | 10/1975 | Hossom et al. |

(Continued)

FOREIGN PATENT DOCUMENTS
WO     03/044217 A2     5/2003
(Continued)

OTHER PUBLICATIONS
International Search Report from corresponding International Application No. PCT/US2007/020654.

(Continued)

*Primary Examiner* — Brian J Sines
(74) *Attorney, Agent, or Firm* — Lerner, David, Littenberg, Krumholz & Mentlik, LLP

(57) ABSTRACT

Various embodiments of the present invention provide, for example, a system and method for automatically adjusting the inoculum level of a sample. Certain embodiments of the present invention may measure a concentration of particles present in a preliminary sample using a sensor device and determine an amount of diluent to be added to or removed from a sample container to prepare a sample having a selected concentration of particles, corresponding to a selected inoculum level. Embodiments of the present invention may also automatically add or remove the diluent using an automated fluidics system so as to prepare a sample having the selected particle concentration. Once the selected particle concentration is achieved and verified, some embodiments may also remove at least a portion of the sample from the sample container such that the container contains a selected volume of the sample.

10 Claims, 13 Drawing Sheets

U.S. PATENT DOCUMENTS

| | | | |
|---|---|---|---|
| 3,987,808 A * | 10/1976 | Carbonell et al. | 137/3 |
| 4,129,381 A | 12/1978 | Wied et al. | |
| 4,169,125 A | 9/1979 | Rodriguez et al. | |
| 4,298,570 A | 11/1981 | Lillig et al. | |
| 4,338,279 A | 7/1982 | Orimo et al. | |
| 4,522,493 A | 6/1985 | Tamagawa et al. | |
| 4,933,147 A | 6/1990 | Hollar et al. | |
| 5,540,890 A | 7/1996 | Clark et al. | |
| 5,578,494 A | 11/1996 | Clark et al. | |
| 5,731,211 A * | 3/1998 | Ohlin | 436/179 |
| 5,807,523 A | 9/1998 | Watts et al. | |
| 5,876,668 A * | 3/1999 | Kawashima et al. | 422/64 |
| 5,902,548 A | 5/1999 | Watts et al. | |
| 6,027,691 A | 2/2000 | Watts et al. | |
| 6,096,272 A | 8/2000 | Clark et al. | |
| 6,653,150 B1 | 11/2003 | Reed | |
| 7,578,978 B2 | 8/2009 | Justin et al. | |
| 2002/0155516 A1 | 10/2002 | Dunfee et al. | |
| 2008/0175760 A1 | 7/2008 | Justin et al. | |

FOREIGN PATENT DOCUMENTS

| | | |
|---|---|---|
| WO | 2006/012454 A1 | 2/2006 |

OTHER PUBLICATIONS

European Search Report from corresponding European Patent Application No. 07838789.1.

* cited by examiner

DEVICE FOR AUTOMATICALLY ADJUSTING THE BACTERIAL INOCULUM LEVEL OF A SAMPLE

CROSS-REFERENCE TO RELATED APPLICATIONS

This application is a divisional of U.S. patent application Ser. No. 11/691,662, filed Mar. 27, 2007, which claims the benefit of the filing date of the U.S. Provisional Application No. 60/847,244, filed Sep. 26, 2006, the disclosures of which are incorporated herein by reference.

FIELD OF THE INVENTION

The various embodiments of the present invention relate generally to devices for preparing bacteria samples having a standard selected inoculum level characterized for example, by a selected particle concentration.

BACKGROUND OF THE INVENTION

Micromethods for the biochemical identification of microorganisms have been utilized for many years. For example, several early publications reported the use of reagent-impregnated paper discs and micro-tube methods for differentiating enteric bacteria. Furthermore, interest in miniaturized bacterial identification systems led to the introduction of several commercial systems in the late 1960's. These early miniaturized biochemical identification systems provided advantages such as requiring little storage space, providing extended shelf life, providing standardized quality control, and being relatively easy to use.

The modern broth microdilution test used today has origins in the tube dilution test used as early as 1942 to determine in vitro antimicrobial susceptibility testing (AST) of bacterial isolates from clinical specimens. The broth dilution technique involves exposing bacteria to decreasing concentrations of antimicrobial agents in liquid media by serial two-fold dilution. The lowest concentration of an antimicrobial agent in which no visible bacterial growth occurs is defined as the minimal inhibitory concentration (MIC). The MIC is the standard measure of antimicrobial susceptibility.

The introduction in 1956 of a microtitrator system, using calibrated precision spiral wire loops and droppers for making accurate dilutions rapidly, allowed the development of a serial dilution AST test. The microtitrator system was accurate and allowed the reduction in volumes of antimicrobial agents. The term "microdilution" appeared in 1970 to describe MIC tests performed in volumes of 0.1 mL or less of antimicrobial solution.

Several commercially-available systems automate the microdilution process for MIC/AST testing. For example, the assignees of the various embodiments of the present invention provide a panel-based system (available commercially as the PHOENIX™ ID/AST System) capable of performing 100 AST and bacterial identification tests at one time. Such systems include a disposable comprising a sealed and self-inoculating molded polymer tray having 136 microwells containing dried reagents. The tray includes: (1) a bacterial identification (ID) side including dried substrates for bacterial ID; and (2) an AST side having varying concentrations of antimicrobial agents, as well as growth and fluorescent controls at appropriate microwell locations.

In such ID/AST systems, the bacterial ID side utilizes a series of chromogenic and fluorogenic biochemical tests to determine the identification of a bacterial organism. Both growth-based and enzymatic substrates are employed to cover different types of reactivity within the range of taxa that may be present in a given sample. These ID tests are based on microbial utilization and subsequent degradation of substrates detected by various indicator systems. Acid production is indicated by a change in phenol red indicator when an isolate is able to utilize a carbohydrate substrate. Furthermore, chromogenic substrates produce a yellow color upon enzymatic hydrolosis of either p-nitrophenyl or p-nitroanilide compounds. Enzymatic hydrolosis of fluoregenic substrates results in the release of a fluorescent coumarin derivative. Bacterial organisms that utilize a specific carbon source reduce the resazurin-based indicator. In addition, other tests are provided on the bacterial ID side to detect the ability of a bacterial organism to hydrolyze, degrade, reduce, or otherwise utilize a given substrate present in the microwells of the bacterial ID side.

Furthermore, the AST side of panel-based systems utilizes broth-based microdilution. For example, the PHOENIX™ system utilizes a redox indicator for the detection of organism growth in the presence of a given antimicrobial agent. Continuous measurements of changes to the indicator, as well as bacterial turbidity measurements (as described further herein) may be used in the determination of bacterial growth. Each AST panel configuration contains several antimicrobial agents with a wide range of two-fold doubling dilution concentrations. Organism ID is used in the interpretation of MIC values of each antimicrobial agent.

Such panel-based systems are conventionally provided as a disposable component of an overall ID/AST system (such as the PHOENIX™ system, for example). In such systems, the disposable panels must be exposed to a sample having a selected organism density (defined, for example, by the turbidity of the sample relative to the McFarland (McF) scale). For example, the PHOENIX™ system often utilizes panels that have been inoculated with a targeted organism density of either 0.25 McF or 0.5 McF.

Thus, the effective use of ID/AST systems requires the manual preparation of a panel inoculum having a selected concentration of particles (expressed as a turbidity, for example) that is standardized relative to the McFarland scale. Therefore, improvements in inoculum preparation and handling are desirable.

SUMMARY OF THE INVENTION

Embodiments of the present invention may include a system for automatically preparing a sample (such as an inoculum, for example) having a selected concentration of particles (corresponding to a selected bacterial density, for example) and/or a selected volume. In one embodiment, the system comprises a fluidics system configured for receiving a sample container containing a preliminary sample, wherein the fluidics system is further configured for adding a diluent to the sample container and/or removing at least a portion of the preliminary sample from the sample container. The system also comprises a sensor device (such as a nephelometer, for example) configured for measuring a concentration of particles in the preliminary sample and a controller device in communication with the fluidics system and the sensor device. The controller device may be configured for receiving the measured concentration of particles from the sensor device and determining an amount of diluent to be added to the sample container and/or an amount of the preliminary sample to be removed from the sample container to prepare the sample having the selected concentration of particles (which may be expressed, in some embodiments, as a turbidity measurement). The controller device may be further configured for controlling the fluidics system to add the determined amount of diluent to the sample container and/or remove the determined portion of the preliminary sample from the sample container so as to prepare the sample having the selected concentration of particles. Furthermore, the controller device may be further configured for controlling the fluidics system to remove at least a portion of the sample from the sample container such that the sample container contains the sample having the selected volume. In some embodiments, the controller device may comprise a user interface configured for receiving a user input comprising at least one of the selected concentration of particles and/or the selected volume of the sample.

In some embodiments, the system may be further configured for receiving a testing container corresponding to the sample container. According to such embodiments, the fluidics system may be further configured for transferring at least a portion of the sample having the selected concentration of particles and/or the selected volume to the testing container. Furthermore, in some such embodiments, the fluidics system may be further configured for dispensing an indicator substance in the testing container and subsequently mixing at least a portion of the sample and the indicator substance in the testing container.

In some system embodiments, the fluidics system may be configured for mixing the preliminary sample and/or the completed sample. For example, in some embodiments, the fluidics system may be further configured for mixing the preliminary sample before determining the concentration of particles suspended therein. The fluidics system may also be further configured for mixing the sample having the selected concentration of particles prior to removing at least a portion of the sample from the sample container.

Some system embodiments may further comprise a robotic system in communication with the controller device. The robotic system may be configured for moving at least one of the sample container, the testing container, the fluidics system, and the sensor device relative to one another. In some such embodiments, the system may further comprise a rack defining an ID aperture configured for receiving the sample container and a testing aperture configured for receiving the testing container. In some system embodiments, at least one of the sample container and the rack may comprise a unique indicator affixed thereto, wherein the unique indicator corresponds to an identity of the preliminary sample and/or a selected concentration of particles present in the prepared sample. In various system embodiments, the unique indicator may include, but is not limited to: a bar code; an alphanumeric label; an RFID label; and other indicator that may be readable, for example, by downstream processing elements such as an interface configured for transferring a prepared sample to an identification and anti-microbial susceptibility testing system, as described further herein.

In some system embodiments, the robotic system may be further configured to receive the rack for moving at least one of the sample container and the testing container relative to the fluidics system and the sensor device. For example, in some system embodiments, the robotic system may be configured for moving through a range of motion defined at least in part by an X-axis, a Y-axis, and a Z-axis. In such embodiments, the robotic system may comprise a shuttle device configured for moving the rack along the X-axis.

In some system embodiments comprising a rack defining an ID aperture configured for receiving the sample container, the rack may further comprise a sample container receptacle configured for receiving the sample container, wherein the sample container receptacle is slidably disposed in the ID aperture. In some such embodiments, the shuttle device may comprise a floor defining a sensor device aperture located at an analysis position (along the X-axis, for example). Furthermore, according to such embodiments, the sensor device may be disposed within the sensor device aperture such that as the rack is moved to the analysis position, the ID aperture is substantially co-located with the sensor device aperture. Therefore, the sample container receptacle may be inserted into the sensor device aperture and adjacent to the sensor device such that the sensor device is capable of measuring the concentration of particles in the preliminary sample contained in the sample container. In some such embodiments, the rack may further comprise a biasing element operably engaged between the rack and the sample container receptacle, configured for biasing the sample container receptacle towards a top surface of the rack. In some such embodiments, the system may further comprise a robotic device configured for operably engaging the sample container receptacle and/or urging the sample container receptacle towards a bottom surface of the rack and into the sensor device aperture when the rack is moved to the analysis position.

In some system embodiments, comprising a robotic system, the system may further comprise a dispensing tip station comprising a plurality of disposable dispensing tips. In such embodiments, the robotic system may be configured for automatically replacing a dispensing tip operably engaged with the fluidics system with at least one of the plurality of disposable dispensing tips after preparing the sample having the selected concentration of particles and/or the selected volume.

In some system embodiments, the robotic system may further comprise a first robotic device comprising a first fluidics head in fluid communication with the fluidics system. The first robotic device may be configured for moving along at least one of the Y-axis and the Z-axis such that the first fluidics head is capable of adding the diluent to the sample container and/or removing at least a portion of the preliminary sample from the sample container as the shuttle device moves the rack to a filling position along the X-axis.

Furthermore, the robotic system may also comprise a second robotic device configured for carrying the sensor device (which may comprise a nephelometer in some embodiments) along the Z-axis so as to position the sensor device adjacent to the sample container along the Z-axis, such that the sensor device is capable of measuring a concentration of particles suspended in the preliminary sample within the sample container as the shuttle device moves the rack to an analysis position along the X-axis. In some embodiments, the system and/or the second robotic device may further comprise a sheath surrounding the sensor device. According to some such embodiments, the sheath may be configured to cooperate with a channel defined about the ID aperture in the rack to provide a substantially light tight environment about the sample container and the sensor device when the second robotic device positions the sensor device adjacent to the sample container when the rack is moved to the analysis position. The second robotic device may also, in some embodiments, further comprise a second fluidics head in fluid communication with the fluidics system. In such embodiments, the second fluidics head may be configured for adding a diluent to the sample container and/or removing at least a portion of the preliminary sample from the sample container so as to prepare the sample having the selected concentration of particles suspended therein.

According to some system embodiments comprising a second robotic device, the system may further comprise a wash station configured for receiving the sensor device and/or the second fluidics head (wherein one or both of which may be carried by the second robotic device, for example). In such embodiments, the wash station may be further configured for washing at least one of the sensor device and the second fluidics head during and/or between sample-preparation cycles.

Various embodiments of the present invention may also comprise an interface configured for transferring the sample having the selected concentration of particles to an identification and anti-microbial susceptibility testing (ID/AST) system configured for analyzing the sample so as to identify at least one bacterial component of the sample and/or to determine a susceptibility of the at least one bacterial component to an anti-microbial compound. Furthermore, some system embodiments may comprise an ID/AST system configured for analyzing the sample so as to identify at least one bacterial component of the sample and/or determine a susceptibility of the at least one bacterial component to an anti-microbial compound. According to some such embodiments, the interface and/or the integrated ID/AST system may be configured for reading a unique indicator affixed to at least one of the rack and the sample container such that the identified at least one bacterial component may be traceable to the preliminary sample originally contained in a particular sample container and/or rack. As described herein, the unique indicator may also correspond, at least in part, to a selected concentration of particles in the prepared sample.

Various embodiments of the present invention also provide methods (and in some embodiments, corresponding computer program products) for automatically preparing a sample having a selected concentration of particles and/or a selected volume in a sample container containing a preliminary sample. In one embodiment, the method comprises steps for measuring a concentration of particles suspended in the preliminary sample using a sensor device (which may, in some embodiments, comprise a nephelometer) and subsequently determining an amount of diluent to be added to the sample container and/or an amount of the preliminary sample to be removed from the sample container to prepare the sample having the selected concentration of particles using a controller device in communication with the sensor device. Various method embodiments may also comprise steps for adding the determined amount of diluent using an automated fluidics system in communication with the controller and/or removing the determined amount of the preliminary sample from the sample container, so as to prepare the sample having the selected concentration of particles using an automated fluidics system in communication with the controller device. Some method embodiments of the present invention further comprise a step for removing at least a portion of the prepared sample from the sample container using the automated fluidics system, such that the sample container contains a sample having the selected volume. As described herein with respect to the various system embodiments of the present invention, a controller device may comprise a user interface. Therefore, some method embodiments may further comprise a step for receiving a user input comprising at least one of the selected concentration of particles and the selected volume of the sample via a user interface in communication with the controller device.

Some method embodiments further comprise a step for transferring at least a portion of the sample having the selected concentration of particles and/or the selected volume to a testing container corresponding to the sample container using an automated fluidics system. According to some such embodiments, the method may further comprise steps for dispensing an indicator substance in the testing container using the automated fluidics system and mixing the at least a portion of the sample and the indicator substance in the testing container using the automated fluidics system. Some method embodiments may also further comprise various mixing steps using the automated fluidics system. For example, some method embodiments may further comprise steps for mixing the preliminary sample before determining the concentration of particles suspended in the preliminary sample and/or mixing the sample having the selected concentration of particles prior to removing at least a portion of the sample from the sample container.

Some method embodiments may further comprise steps for reducing or preventing the cross-contamination of various sample containers and testing containers. For example, some method embodiments may further comprise replacing a dispensing tip operably engaged with the automated fluidics system with at least one of a plurality of disposable dispensing tips stored in a dispensing tip station, after removing at least a portion of the sample from the sample container. Furthermore, some method embodiments may further comprise washing the sensor device using a wash station configured for receiving the sensor device when it is not in use.

Thus the various embodiments of the present invention provide many advantages that may include, but are not limited to: providing a system and method for automatically preparing a sample having a standardized and substantially accurate concentration of particles suspended therein (characterized as a turbidity measured against the McFarland scale, for example); providing a system and method for preparing multiple samples that reduces or prevents cross-contamination between samples; providing a system and method for preparing multiple samples that is compatible with and/or incorporates existing substantially-automated bacterial identification and AST testing systems and routines.

These advantages, and others that will be evident to those skilled in the art, are provided in the systems and methods of the various embodiments of the present invention.

BRIEF DESCRIPTION OF THE DRAWINGS

Figure 1:
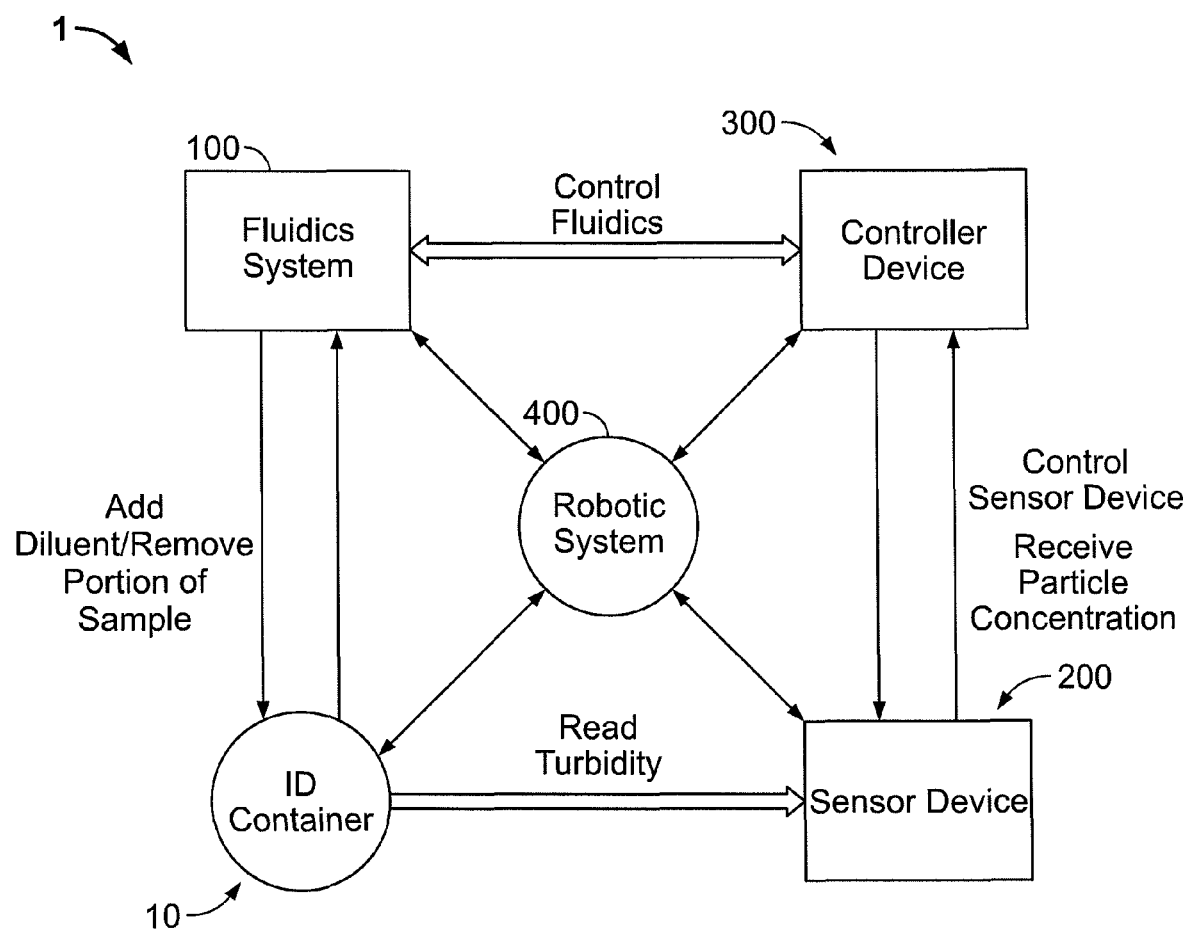
Figure 2:
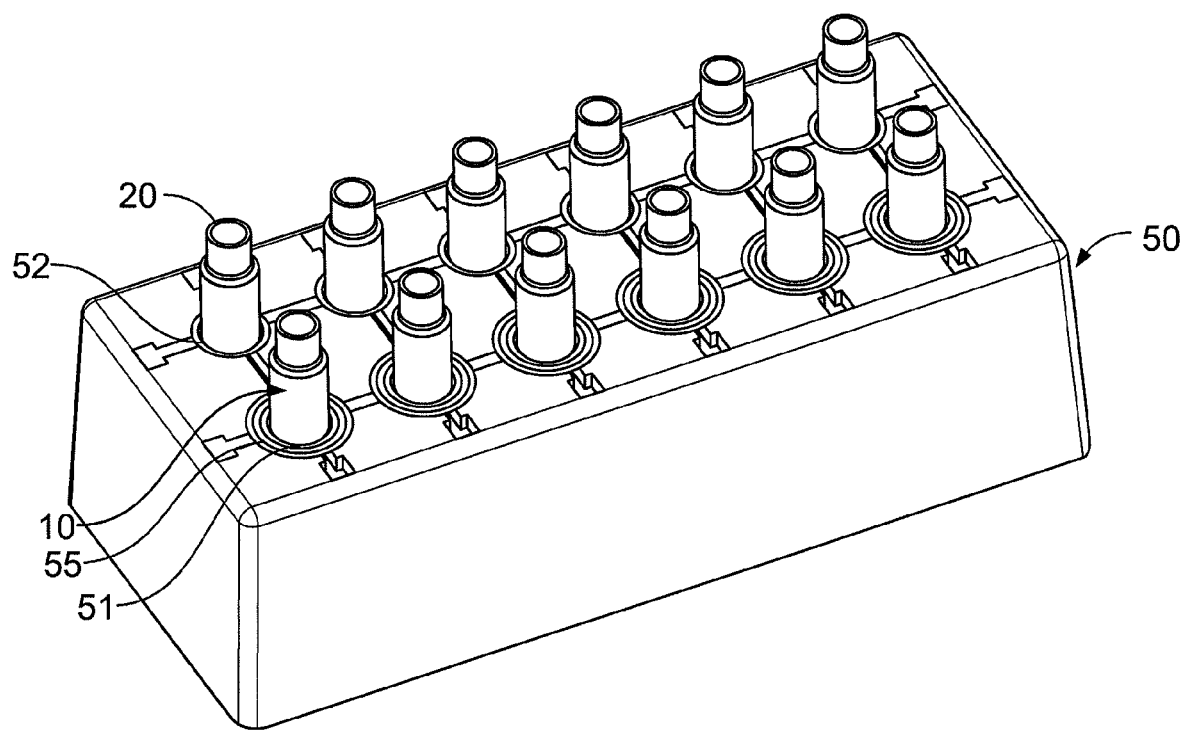
Figure 3:
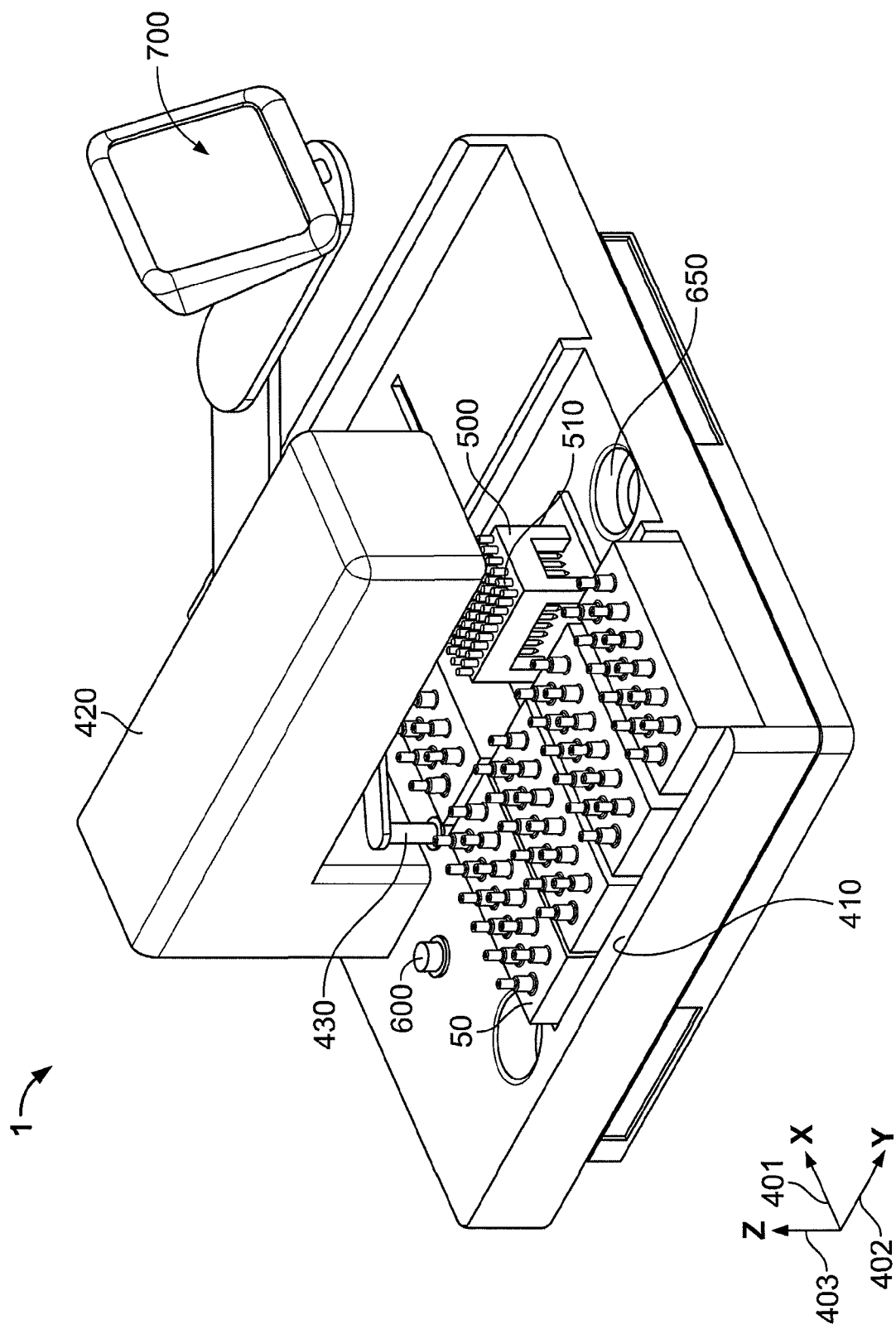
Figure 4:
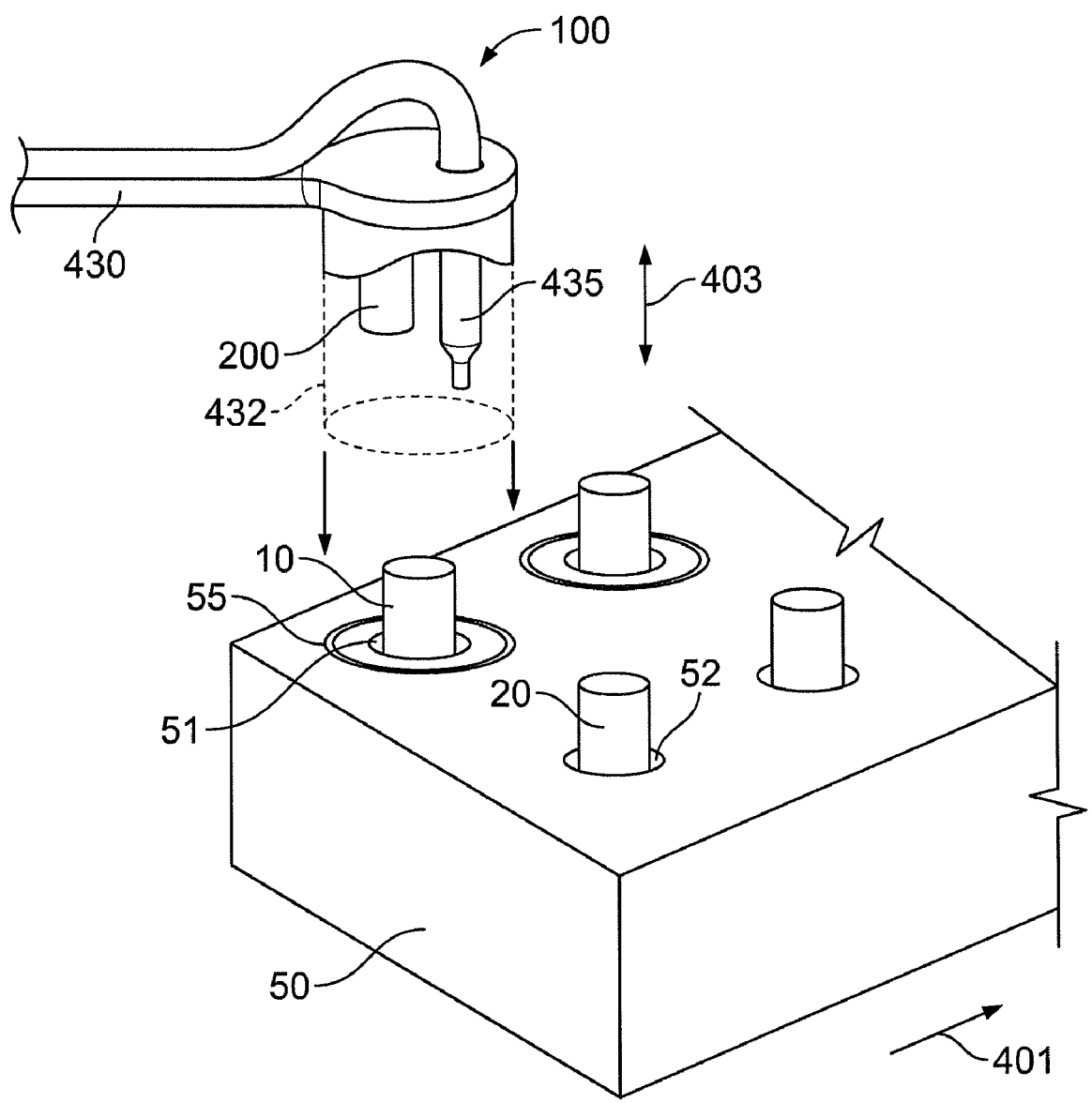
Figure 5:
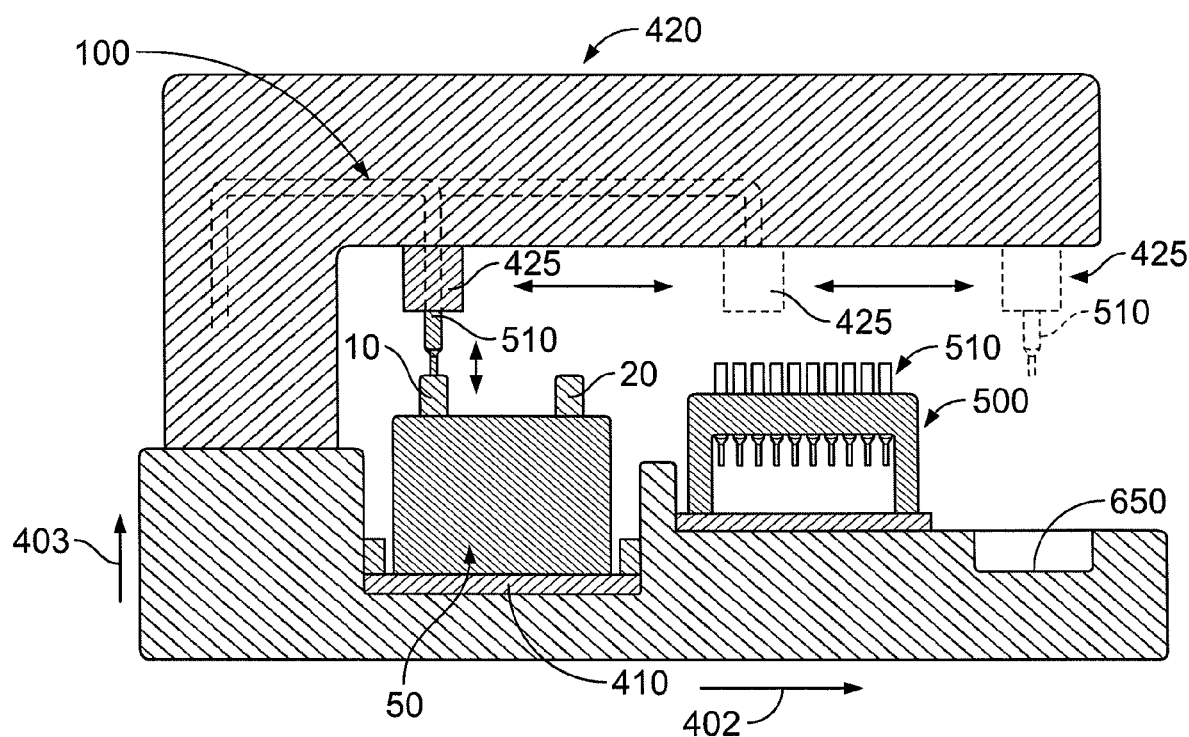
Figure 6:
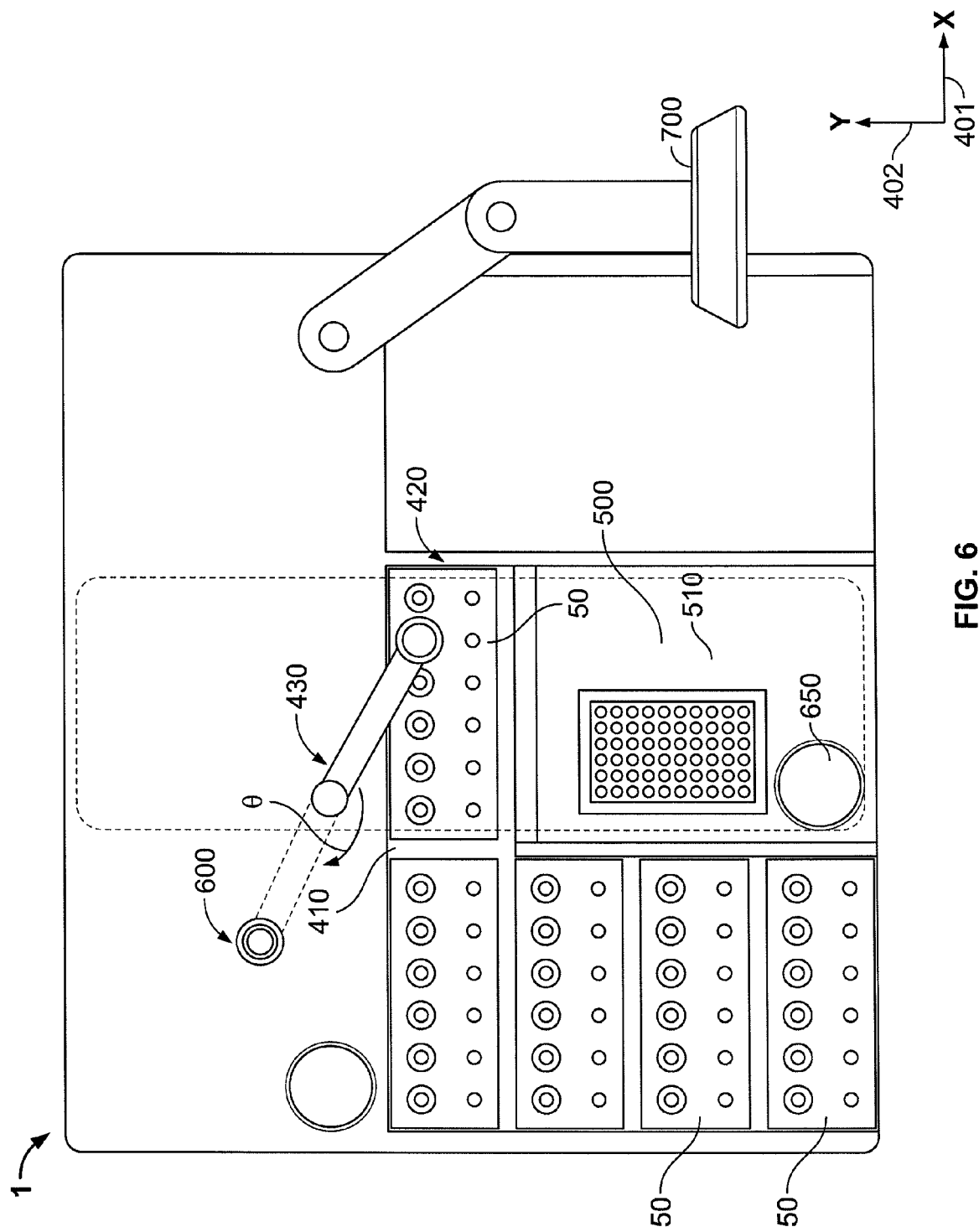
Figure 7:
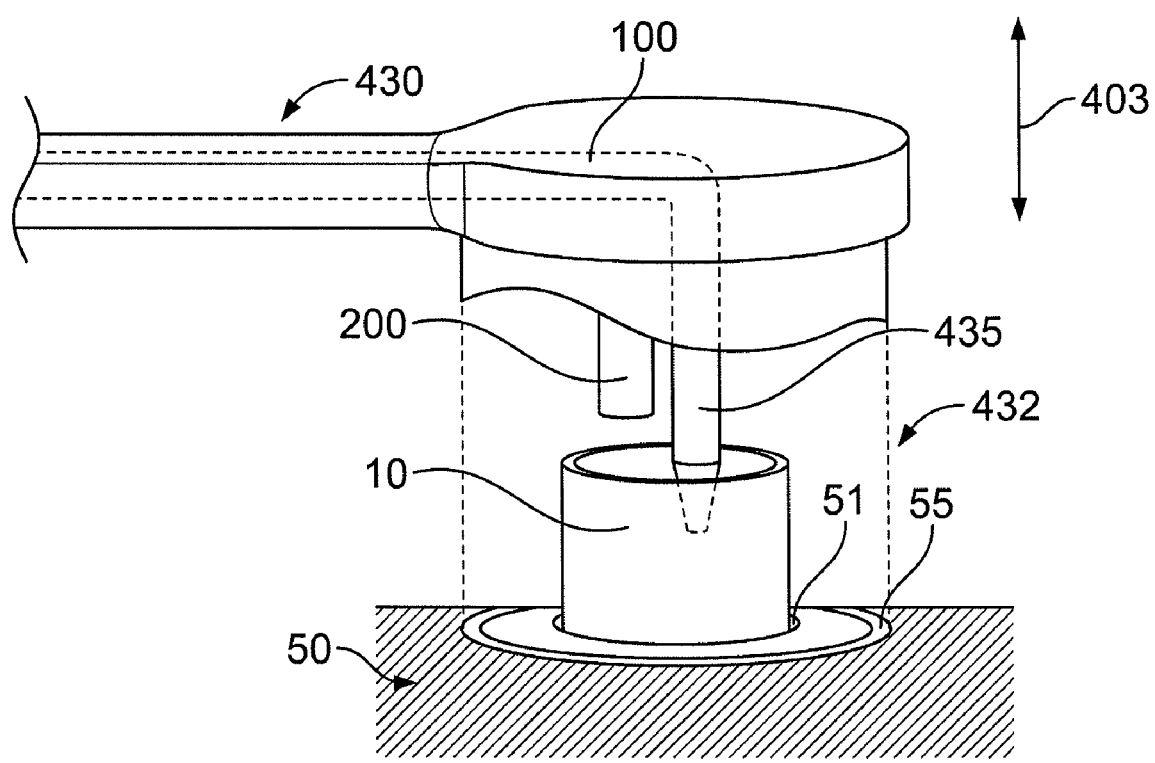
Figure 8:
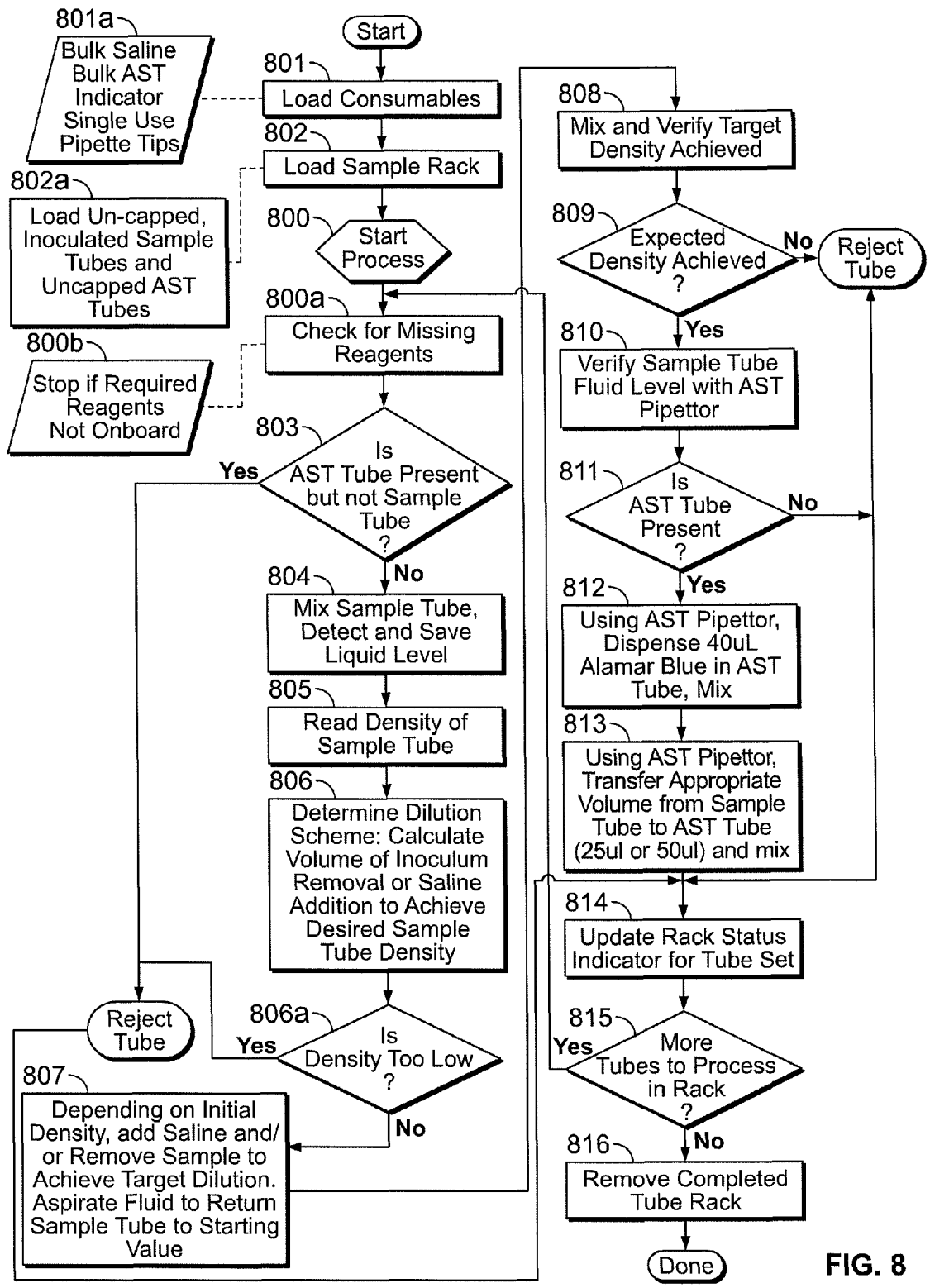
Figure 9:
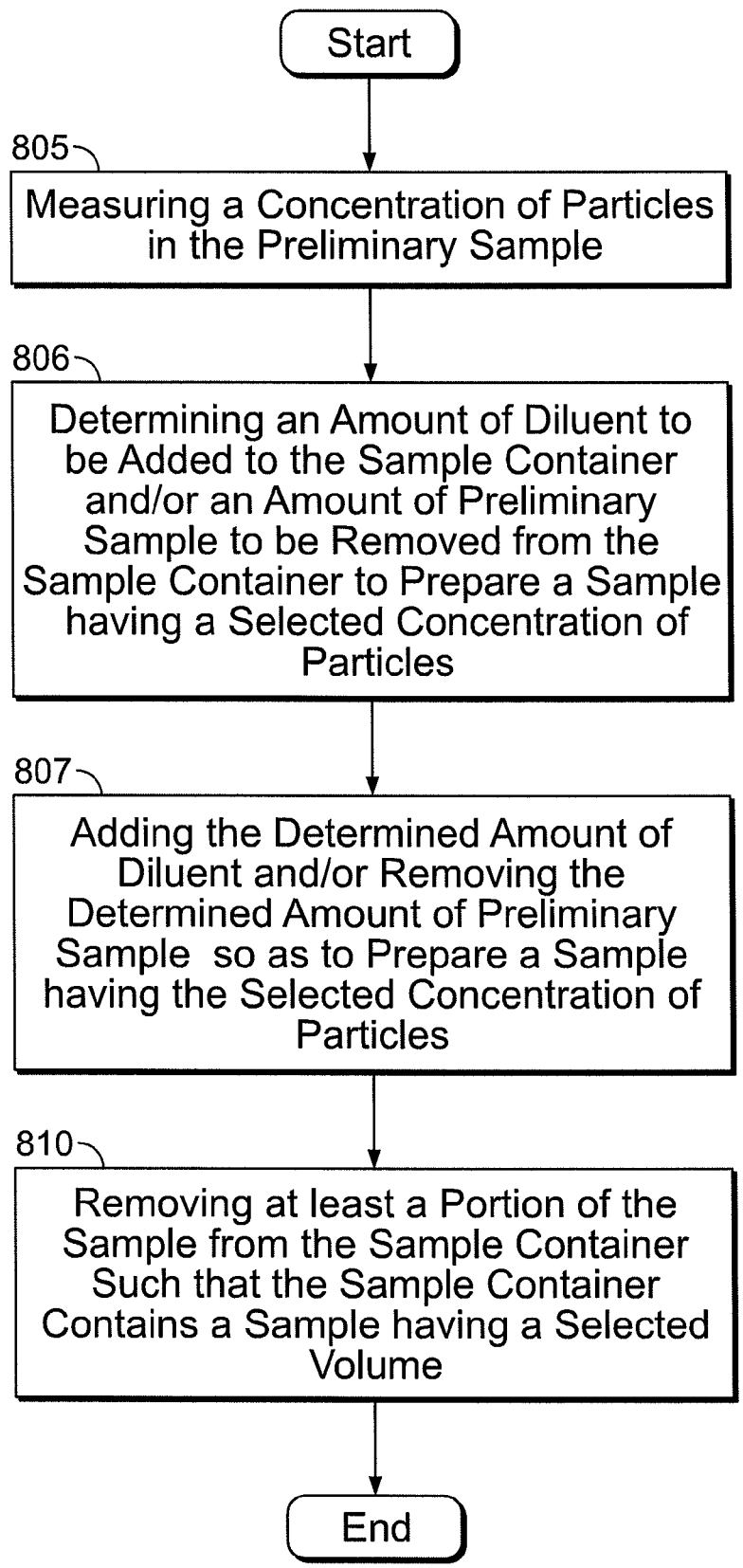
Figure 10:
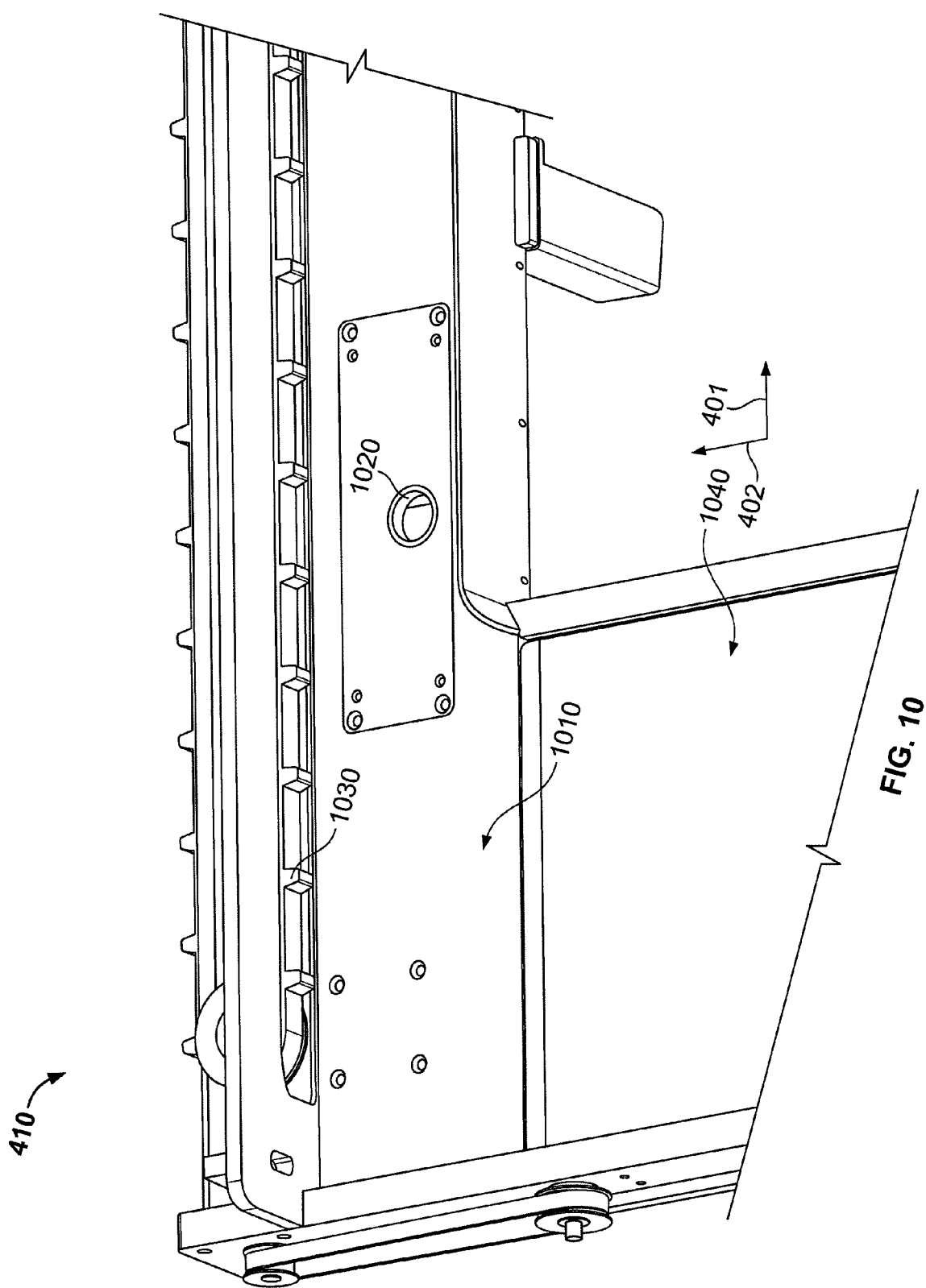
Figure 11:
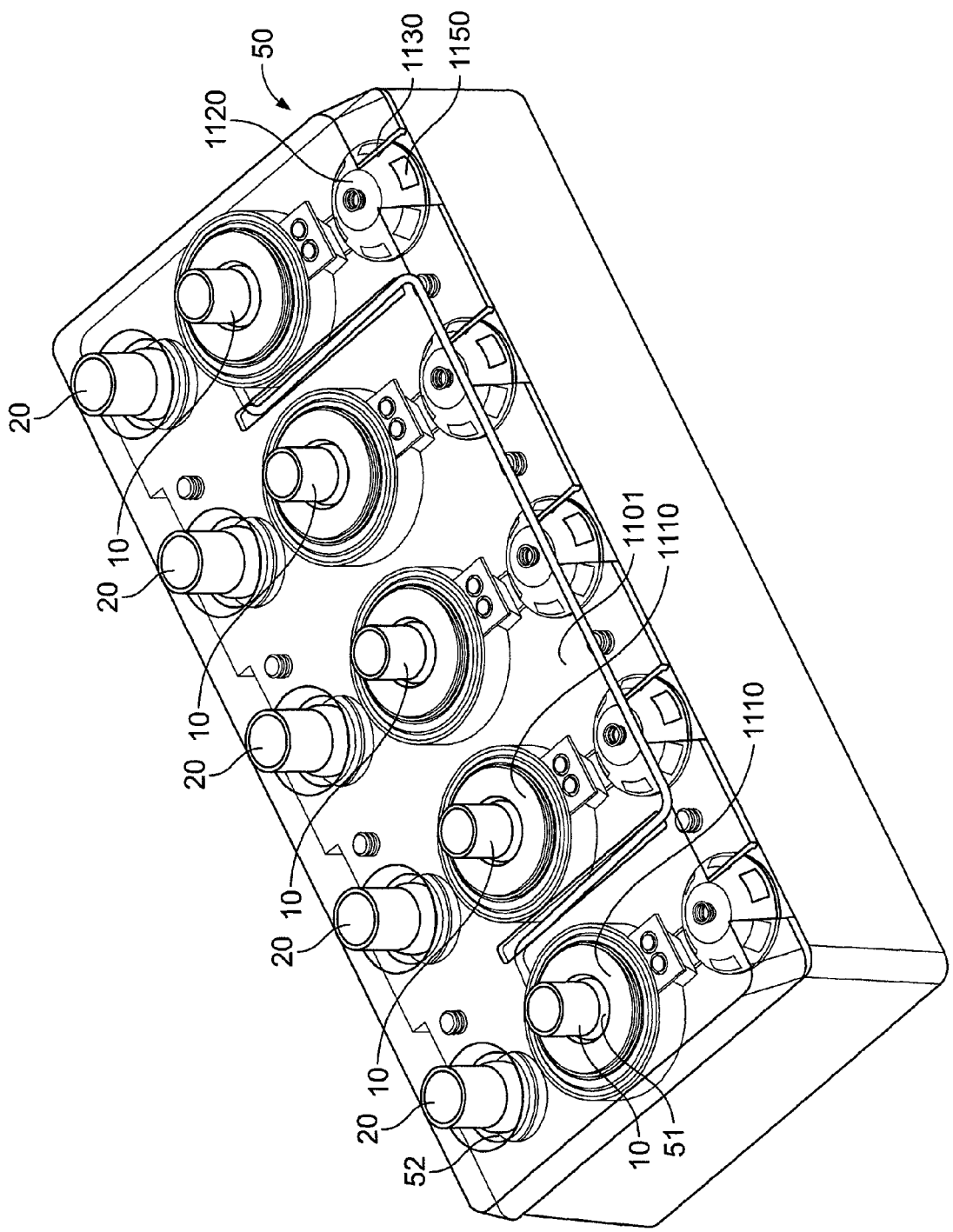
Figure 12:
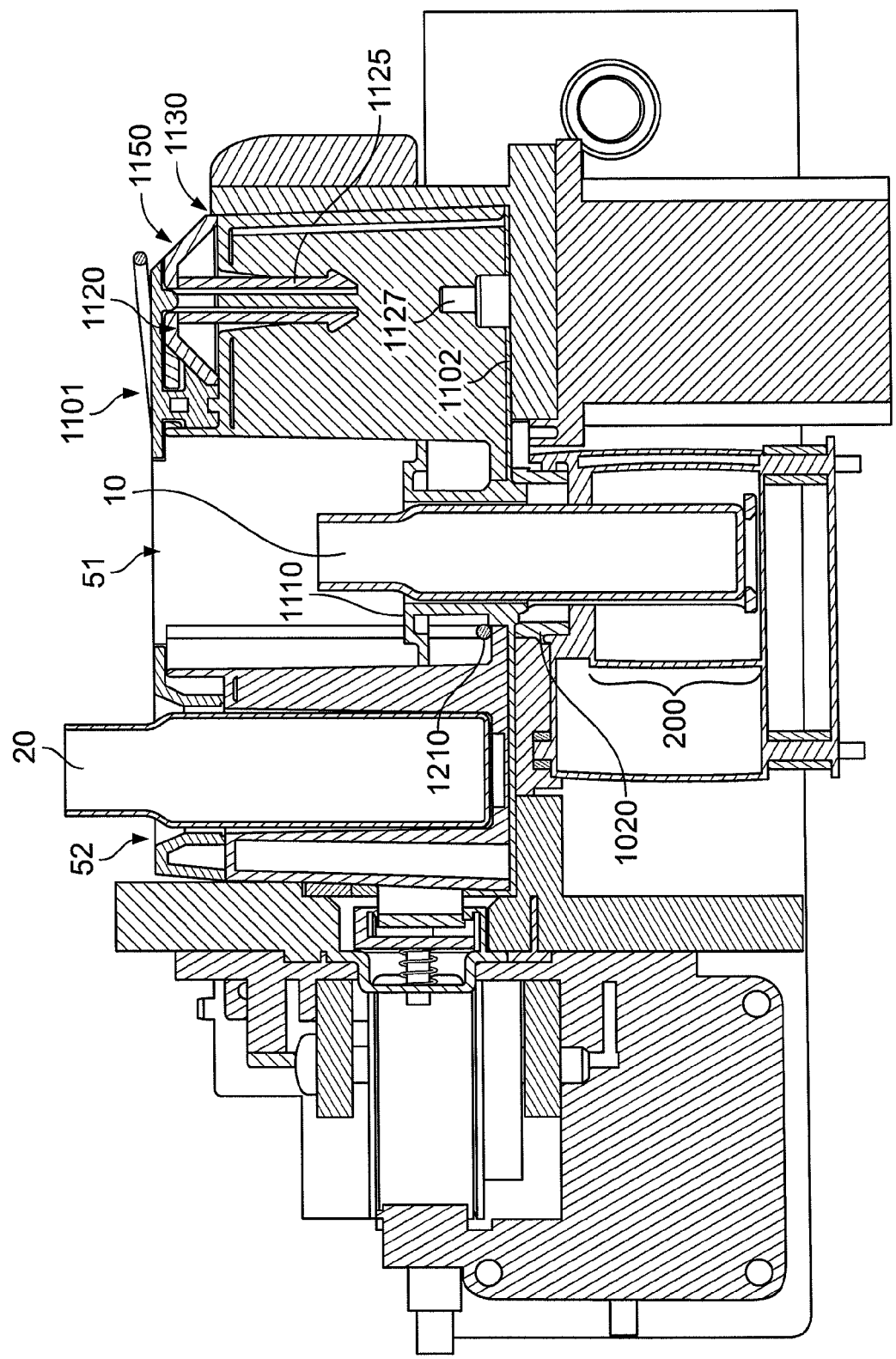
Figure 13:
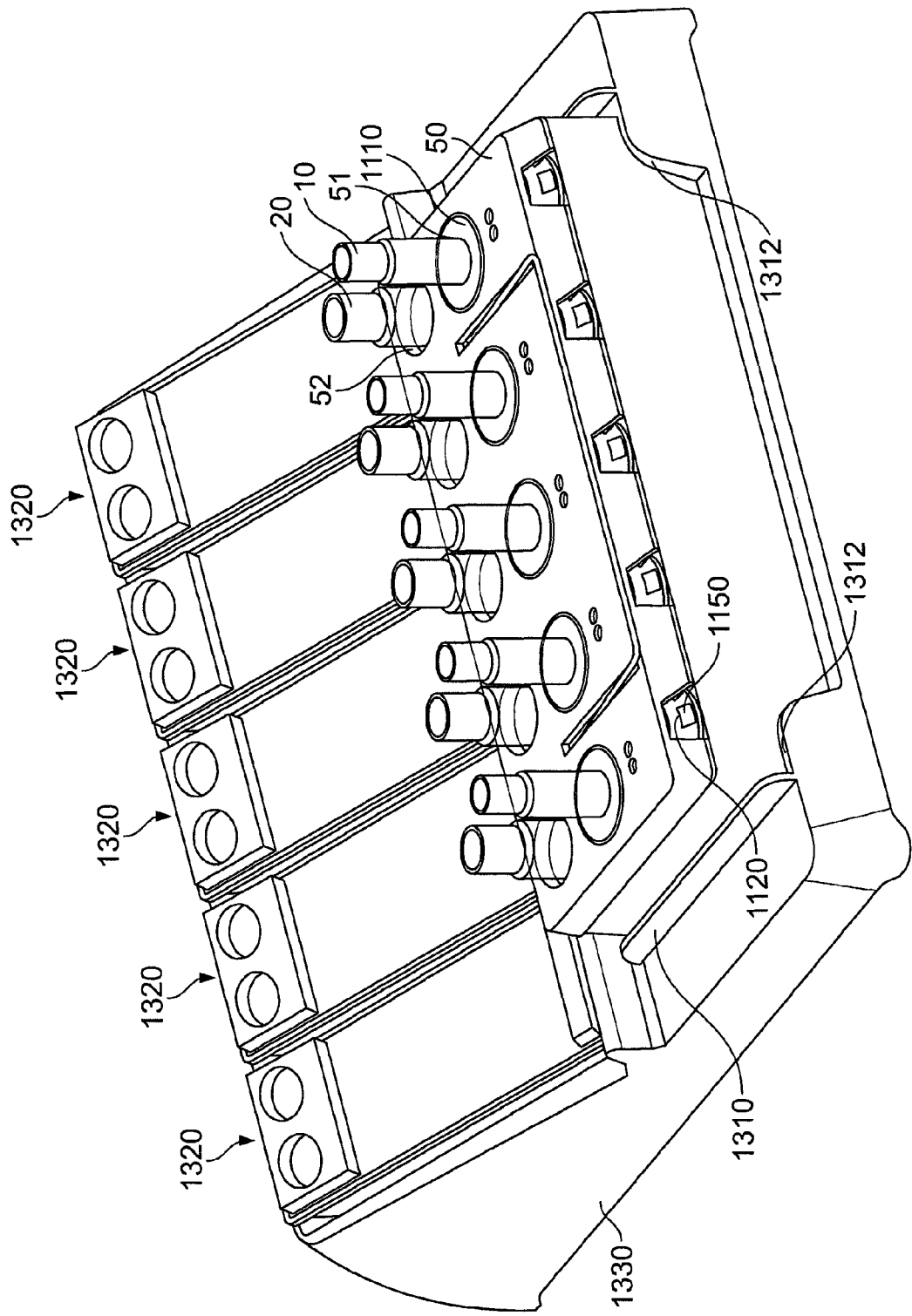

Having thus described various embodiments of the invention in general terms, reference will now be made to the accompanying drawings, which are not necessarily drawn to scale, and wherein:

FIG. 1 shows a non-limiting schematic of the operation of a system for automatically preparing a sample having a selected turbidity level and a selected volume, according to one embodiment of the present invention;

FIG. 2 shows a non-limiting perspective view of a tray configured to carry a plurality of sample containers and a corresponding plurality of testing containers in a system for automatically preparing a sample having a selected turbidity level and a selected volume, according to one embodiment of the present invention;

FIG. 3 shows a non-limiting perspective view of a system for automatically preparing a sample having a selected turbidity level and a selected volume, according to one embodiment of the present invention;

FIG. 4 shows a non-limiting detailed perspective view of the interaction of a second robotic device, carrying a nephelometer and a fluidics head surrounded by a light-shielding sheath, with a channel defined in an sample container tray, according to one embodiment of the present invention;

FIG. 5 shows a non-limiting side-view of a system for automatically preparing a sample having a selected turbidity level and a selected volume, according to one embodiment of the present invention;

FIG. 6 shows a non-limiting top-view of a system for automatically preparing a sample having a selected turbidity level and a selected volume, according to one embodiment of the present invention;

FIG. 7 shows a non-limiting detailed perspective view of a second robotic device, carrying a nephelometer and a fluidics head surrounded by a light-shielding sheath, operably engaged with a channel defined in an sample container tray to form a substantially light-tight environment around the sample container for a turbidity measurement, according to one embodiment of the present invention;

FIG. 8 shows a non-limiting schematic of the steps of a method and computer program product for automatically preparing a sample having a selected turbidity level and a selected volume;

FIG. 9 shows a non-limiting schematic of the steps of a method and computer program product for automatically preparing a sample having a selected turbidity level and a selected volume, comprising steps for measuring turbidity, determining a diluent amount, dispensing a diluent, and removing a portion of a sample, according to one embodiment of the present invention;

FIG. 10 shows a non-limiting perspective view of a shuttle device, according to one embodiment of the present invention, comprising a floor defining a sensor aperture;

FIG. 11 shows a non-limiting perspective view of a rack, according to one embodiment of the present invention, comprising a sample container receptacle configured for receiving the sample container;

FIG. 12 shows a non-limiting cross-sectional view of a rack located an at analysis position such that the sample container receptacle may be lowered in to the sensor device aperture; and FIG. 13 shows a non-limiting perspective view of an interface configured for transferring the sample having the selected concentration of particles to an identification and anti-microbial susceptibility testing system configured for analyzing the sample.

DETAILED DESCRIPTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The various embodiments of the present invention are described herein in the context of an environment for preparing bacterial samples having a standard level characterized by a selected density for use with downstream ID/AST processes that analyze samples placed in ID/AST disposable trays including: (1) a bacterial identification (ID) side including dried substrates for bacterial ID; and (2) an AST side having varying concentrations of antimicrobial agents, as well as growth and fluorescent controls at appropriate microwell locations. However, it should be understood that the various systems 1, methods and computer program products described herein may be utilized for producing a variety of different sample types having a selected particle concentration (characterized by a turbidity measurement, for example) and/or a selected volume. For example, various embodiments of the present invention may be utilized to produce and/or replicate a solution having a selected particle concentration (measured, for example, as a turbidity level relative to a McFarland standard) comprising a preliminary sample of latex particles suspended in a sterile saline diluent. In other embodiments, the automated sensor device 200, fluidics system 100, and controller device 300 may be used to produce and/or replicate a McFarland standard (such as a 0.5 McFarland standard) comprising 0.05 mL of 1.175% barium chloride dehydrate ($BaCl_2.2H_2O$) and 9.95 mL of 1% sulfuric acid ($H_2SO_4$).

Some embodiments of the present invention may comprise a system 1 for automatically preparing a sample having a selected concentration of particles suspended therein and/or a sample having a selected volume that may be optimized for use with downstream processes (such as an ID/AST procedure, for example). As shown generally in FIG. 1, the system 1 may comprise a fluidics system 100 configured for receiving a sample container 10 (see FIG. 2, for example) containing a preliminary sample (such as a bacterial sample taken from one or more media plates). It should be understood that the preliminary sample may be prepared using automated and/or manual processes. For example, in some embodiments, a preliminary sample of inoculum may be prepared for downstream ID/AST processes. According to some such exemplary embodiments, ID/AST panel sample may be prepared by picking bacterial colonies of the same morphology with the tip of a sterile cotton swab from one of several different media plates and manually depositing such colonies in a test tube filled with sterile media. The resulting bacterial samples may then be suspended in a sample container 10 and vortexed for a selected period of time.

As further described herein with respect to FIGS. 4-6, the fluidics system 100 components of the various system embodiments described herein may be further configured for adding a diluent to the 10 and/or removing at least a portion of the preliminary sample from the sample container 10. As described further herein, the fluidics system 100 may comprise a plurality of different fluidics heads 435, 425 in fluid communication with a supply of diluent (such as a sterile saline reservoir, for example) such that the fluidics system 100 is capable of dispensing the diluent to one or more of the sample containers 10 and/or testing containers 20. Furthermore, the fluidics system 100 (and the various fluidics heads 435, 425 in fluid communication therewith) may also be configured to be capable of aspirating, mixing, and/or vortexing the preliminary samples and/or the produced samples having a selected turbidity level during the operation of the system 1. Furthermore, and as further described herein, the fluidics system 100 may also be capable of operably engaging one or more disposable dispensing tips 510 (see FIG. 5 showing a system 1 comprising a dispensing tip station 500 from which a disposable dispensing tip 510 may be "picked" by a first fluidics head 425 operably engaged with a first robotic device 420).

The fluidics system 100 may, in some embodiments, comprise an automated pipettor system that makes use of the disposable dispensing tips 510 to prevent cross-contamination of various ID tubes 10 (and corresponding testing tubes 20). In such embodiments, the pipettor may perform fluid transfer of a diluent from a storage container (such as a reservoir comprising saline solution, for example) to the sample container 10 thereby allowing the preliminary sample (comprising a bacterial sample, for example) to be diluted to a selected concentration of particles (corresponding to a McFarland value). The pipettor may also level the fluid level of the sample container 10 (and/or remove a portion of the sample to achieve a selected volume) and transfer a predetermined amount of the sample having the selected turbidity level from the sample container 10 to an associated testing container 20 (such as an AST container, for example). The pipettor may also be configured to add an indicator substance (i.e. an AST indicator dye) to the testing container 20. In some system 1 embodiments including a fluidics system 100 comprising an automated pipettor, the pipettor may also perform various sample mixing steps or functions by performing various aspirate and dispense cycles. In some embodiments, the fluidics system 100 (comprising an automated pipettor, for example) may also be configured for aspirating the preliminary sample and/or the prepared sample having a selected concentration of particles so as to measure a volume of the sample.

In some embodiments, the fluidics system 100 (which may be embodied as a pipettor system carried by one or more components of the robotic system 400) may comprise one or more sensor tips (such as capacitive pipette tips having capacitive sensors embedded therein for detecting a presence of an ionic fluid (such as the preliminary sample and/or prepared sample)). The sensor tip, in cooperation with the controller device 300 described herein, may be configured for determining a volume of preliminary sample and/or prepared sample in the sample container 10. For example, in some embodiments, such sensor tips may be carried by a component of the robotic system 400 that is capable of moving through a range of motion relative to the Z-axis 403 (see FIG. 4, for example). Because the sensor tip is capable of sensing the presence of the preliminary sample (or other ionic fluids) in the sample container 10, and because the maximum volume of the standard sample container 10 is known (and may be programmed into the controller device 300), the position of the robotic system 400 component carrying the sensor tip along the Z-axis 403 may be indicative of the total volume of preliminary sample and/or prepared sample in the sample container 10. Thus, according to such embodiments, the sensor tip carried by the robotic system 400 (and in communication with the fluidics system 100) may allow for the precise determination of volume within the sample container 10. The determination of a selected volume of the prepared sample may be especially advantageous for preparing samples having both a selected concentration of particles therein as well as a selected volume that is compatible with ID/AST systems configured for determining an identity and/or an antimicrobial susceptibility of the particles suspended in the sample.

Furthermore, the system 1 further comprises a sensor device 200 (see also FIG. 4 showing a sensor device 200 head carried by a second robotic device 430) configured for measuring a concentration of particles suspended in the preliminary sample in the sample container 10. The sensor device 200 may comprise an analog and/or digital optical instrument configured for measuring a turbidity level of a suspension on a standard scale (such as the McFarland scale, for example). For example, in some embodiments, the sensor device 200 may comprise a nephelometer configured for generating a turbidity measurement. In other embodiments, the sensor device 200 may comprise one or more optical devices configured for measuring at least one of: a scattering parameter; a transmittance; a reflectivity; and/or another optical parameter that may be directly and/or indirectly related to a concentration of particles suspended in the sample. In some embodiments, the sensor device 200 may comprise one or more optical emitters (configured for generating electromagnetic energy in a visible and/or non-visible spectrum and one/or more corresponding optical receivers configured for measuring a transmittance and/or reflectivity of the electromagnetic energy incident on the sample. The sensor device 200 may also, in some embodiments, comprise one or more electronic interfaces for communicating with a controller device 300 so as to be capable of transmitting a measured concentration of particles (expressed in some embodiments as a turbidity value, for example) to the controller device 300. For example, the sensor device 200 may be in wired and/or wireless communication with the controller device 300 via a computer network and/or a direct "hard-wired" connection. In some embodiments, the sensor device 200 may be in communication with the controller device 300 via one/or more interface components (such as RS-232 interfaces, for example). Furthermore, in some system 1 embodiments, the sensor device 200 may be "zeroed" (by placing a substantially pure saline solution in the sample container 10 (see FIG. 7, for example) and/or calibrated to a McFarland standard (by placing a 0.5 and/or 0.25 McFarland standard solution in the sample container 10.

Furthermore, as shown for example in FIGS. 4 and 12 the sensor device 200 may be disposed in various positions relative to other system 1 components of the embodiments of the present invention. For example, in some embodiments, the sensor device 200 may be disposed in a sensor device aperture 1020 (see FIG. 10) defined in a floor 1010 of a shuttle device 410 that may be configured for moving a rack 50 containing one or more sample containers 10 (as described further herein). In other embodiments, the sensor device 200 (and/or a receiver and/or emitter portion thereof) may be carried by one or more robotic devices 430 (as shown in FIG. 4, for example).

As shown schematically in FIG. 1, the system 1 further comprises a controller device 300 in communication with the fluidics system 100 and the sensor device 200. The controller device 300 may be generally embodied as a typical computer system or processing element, including but not limited to: a microprocessor, VLSI, ASIC, etc. The controller device 300 may also comprise one or more of: a storage device (for storing one or more selected turbidity levels, standard or calibration turbidity levels, and/or selected volumes, for example); a user interface 700 (comprising a display, keyboard and/or mouse interface, for example); and one/or more network interfaces configured to allow the controller device 300 to communicate with a wired or wireless network and/or one or more external computer systems.

Furthermore, as shown generally in FIG. 1, the controller device 300 may be configured for receiving the measured concentration of particles suspended in the preliminary sample from the sensor device 200. Furthermore, the controller device 300 (and/or a processor device included therein) may be further configured for determining an amount of diluent to be added to the sample container 10 and/or an amount of the preliminary sample to be removed from the sample container in order to prepare a sample having the selected concentration of particles (which may be pre-defined by the controller device 300 and/or received by the controller device 300 via a user interface 700). For example, the controller device 300 (and/or a processor included therein) may be configured for calculating the amount of diluent that should be added to the sample container 10 and/or an amount of the preliminary sample to be removed from the sample container in order to prepare a sample having a selected turbidity (based at least in part on the relationship of the measured turbidity to the turbidity of a McFarland standard, for example).

Furthermore, the controller device 300 may also be further configured for controlling the fluidics system 100 (and one or more fluidics heads 425, 435 and/or automated pipettors in fluid communication therewith) to add the determined amount of diluent to the sample container 10 and/or to remove the determined amount of the preliminary sample from the sample container 10 so as to prepare the sample having the selected turbidity level. Furthermore, the controller device 300 may be further configured for controlling the fluidics system 100 to remove (via aspiration, for example) at least a portion of the sample from the sample container 10 such that the sample container 10 contains the selected volume of the sample having the selected turbidity. As described herein, the controller device 300 may also be in communication with one or more components 410, 420, 430 of a robotic system that may be configured to carry and/or manipulate various parts of the fluidics system 100 (and/or various fluidics heads 425, 435) in relation to the sample container 10.

As shown generally in FIG. 5, in some system 1 embodiments, the fluidics system 100 may be further configured for receiving a testing container 20 (such as an antimicrobial susceptibility testing (AST) container, for example) corresponding to the sample container 10 (see also FIG. 2, showing a tray 50 configured to carry a plurality of sample containers 10 and a corresponding plurality of testing containers 20). The fluidics system 100 (and, in some embodiments, a first fluidics head 425 in fluid communication therewith and carried by a first robotic device 420) may be further configured for transferring at least a portion of the sample having the selected turbidity level and the selected volume from the sample container 10 to the testing container 20. In some system 1 embodiments, the fluidics system 100 may be further configured for dispensing an indicator substance (such as an optimized colorimetric redox indicator, for example) in the testing container 20 and subsequently mixing the at least a portion of the sample and the indicator substance in the testing container 20. In such embodiments, the system 1 may further comprise a reservoir containing a supply of indicator substance that may be removed and/or dispensed by an automated pipettor device and/or a fluidics head 425 carried by a first robotic device 420. Furthermore, the various components of the fluidics system 100 may also mix the indicator substance with the sample by performing a series of aspirate and dispense cycles.

The fluidics system 100 may also be configured for performing a number of other mixing functions during the operation of the various embodiments of the system 1. As described herein, the fluidics system 100 may, in some embodiments, perform such mixing functions by performing a number of aspirate and dispense cycles with the sample container 10 and/or the testing container 20. For example, in some system embodiments, the fluidics system 100 may be further configured for mixing the preliminary sample in the sample container 10 before determining the turbidity level of the preliminary sample (see, for example, step 804 shown in the system 1 and/or method flow chart of FIG. 8). In other system 1 embodiments, the fluidics system may be further configured for mixing the sample having the selected turbidity level prior to removing at least a portion of the sample from the sample container 10 (see, for example, step 808 shown in FIG. 8).

As shown generally in FIGS. 1, 3, 5 and 6, the system 1 may further comprise various components 410, 420, 430 of a robotic system 400 in communication with the controller device 300. As shown schematically in FIG. 1, the robotic system 400 may be configured for moving at least one of the sample container 10, the testing container 20, the fluidics system 100, and the sensor device 200 relative to one another.

In order to facilitate the positioning and movement of a discrete number of sample containers 10 (and, in some embodiments, corresponding testing containers 20 using the robotic system 400, the system 1 may also comprise a rack 50 as shown in FIG. 2. In some embodiments, the rack 50 defines an ID aperture 51 configured for receiving the sample container 10 and a testing aperture 52 configured for receiving the testing container 20.

In some system 1 embodiments, at least one of the rack 50, the sample container 10, and the testing container 20 may comprise a unique indicator affixed thereto, wherein the unique indicator corresponds to the selected concentration of particles and/or to an identity of the preliminary sample contained within a particular container 10, 20 In such embodiments, the unique indicator may comprise a machine-readable indicator and/or various other unique indicators that may include, but are not limited to: a bar code; an alphanumeric label; an RFID label; and/or combinations of such indicators. As described further herein, such unique indicators may be read by at an interface 1310 station (see FIG. 13) and/or by a downstream ID/AST system such that the sample prepared and/or analyzed by the various system 1 embodiments of the present invention may be traceable to a particular rack 50 and/or sample container 10 (that may be further traceable back to a particular bacterial sample, for example, via the unique indicator). In embodiments wherein the unique indicators comprise machine-readable indicators (such as bar code and/or RFID-encoded information) the system 1 (and/or the controller device 300 thereof) may be configured for periodically reading the unique indicator for tracking the progress of a particular sample and/or bacterial sample as it is processed by the various system 1 embodiments of the present invention.

As shown in FIG. 11, the unique indicator 1150 may be operably engaged with a rotatable status wheel 1120 that may be further operably engaged with the rack 50. The status wheel 1120 may comprise a plurality of sides each comprising a unique indicator 1150 corresponding, for example, to a particular selected concentration of particles (as measured, for example, by the sensor device 200 when the rack 50 is advanced to an analysis position (as shown generally in FIG. 12)). The rack 50 may define a status window 1130 such that only one of a plurality of unique indicators 1150 are visible to a user (and/or a downstream indicator reader (such as a bar-code scanner, for example)) at any one time. As shown in FIG. 12, the system 1 may comprise an rotating actuator 1127 configured for selectively engaging a stem 1125 of the status wheel 1120 when the rack 50 is at a particular position within the system 1 (such as an analysis position with respect to the sensor device 200 (as shown generally in FIG. 12)). The rotating actuator 1127 may be in communication with the sensor device 200 (via the controller device 300, for example) such that the rotating actuator 1127 may be responsive to the concentration of particles (expressed in some embodiments as a turbidity) determined by the sensor device 200. Therefore, in some embodiments, the rotating actuator 1127 may be configured for rotating the status wheel 1120 relative to the rack 50 such that the unique indicator 1150 that is visible via the status window 1130 defined in the rack 50 substantially corresponds to the selected concentration of particles (expressed, for example, as turbidity on the McFarland Scale) in the prepared sample.

As shown generally in FIG. 6, the robotic system 400 (and/or a shuttle device 410 thereof, comprising an X-axis 401 shuttle device) may be further configured to receive the rack 50 for moving at least one of the sample container 10 and the testing container 20 relative to the fluidics system 100 and the sensor device 200. For example, as shown generally in FIG. 6, the robotic system 400 may comprise a shuttle device 410, comprising register devices (such as indentations sized for receiving the rack 50) for receiving and carrying the rack 50 along the X-axis 401 of the system 1 to one or more positions relative to a first robotic device 420 and/or a second robotic device 430 as described further herein, such that these various components of the robotic system 400 may operate sequentially on the sample container 10 (and the sample contained therein) to produce a sample having a selected concentration of particles and/or a selected volume.

As shown generally in FIG. 10 the shuttle device 410 may comprise a drive belt 1030 configured for carrying the rack 50 along the X-axis 401 of the system 1 to one or more positions relative to a first robotic device 420 and/or a second robotic device 430 as described further herein. The shuttle device 410 may also comprise one or more conveyors 1040 configured for advancing the rack 50 in an entrance queue along the Y-axis 402, for example. In some embodiments the shuttle device 410 (and associated conveyors 1040) may carry the rack 50 in a substantially "U-shaped" path from entrance queue (shown in the left side of the system 1 embodiment shown in FIG. 6, for example) to the X-axis 401 pathway defined by the shuttle device 410, and finally to an exit queue (shown in the right side of the system 1 embodiment shown in FIG. 6, for example).

As shown generally in FIG. 10, in some embodiments, the shuttle device 410 may comprise a floor 1010 defining a sensor device aperture 1020 located at an analysis position along the X-axis 401. According to such embodiments (and as shown in further detail in the cross-sectional view of FIG. 12, for example), the sensor device 200 may be mounted and/or disposed within the sensor device aperture 1020 such that as the rack 50 is moved to the analysis position along the system's X-axis 401 the sample container 10 may be lowered into the sensor device aperture 1020 via the ID aperture 51 (which, in some embodiments, may extend completely through the thickness of the rack 50 assembly (as shown in FIG. 12, for example). Referring to FIGS. 11 and 12, in some such embodiments, the rack 50 may comprise a sample container receptacle 1110 configured for receiving the sample container 10. As shown particularly in FIG. 12, the sample container receptacle 1110 may be slidably disposed in the ID aperture 51 such that the sample container 10 may be urged downward through the rack 50 and into the sensor device aperture 1020 such that the sensor device 200 may measure a concentration of particles suspended in the sample contained within the sample container 10. In some such embodiments, the rack 50 may further comprise a biasing element 1210 operably engaged between the rack 50 and the sample container receptacle 1110. In some embodiments, the biasing element 1210 may comprise a spring configured for biasing the sample container receptacle 1110 towards a top surface 1101 of the rack 50.

In some embodiments, the system may further comprise a robotic device (such as, for example, the second robotic device 430 shown in FIG. 4). The robotic device may be configured for operably engaging the sample container receptacle 1110 so as to urge the sample container receptacle 1110 (and the sample container 10 held therein) towards a bottom surface 1102 of the rack 50 and into the sensor device aperture 1020 defined in the floor 1010 of the shuttle device 410 when the rack 50 is moved to the analysis position. In such embodiments, because the sensor device 200 is substantially enclosed in a low-light environment (within the sensor device aperture 1020, for example), a substantially light-tight environment may be established about the sensor device 200 and the sample container 10 when the robotic device urges the sample container receptacle 1110 downward and into the sensor device aperture 1020. Thus, according to such embodiments, the second robotic device 430 need not carry the sensor device 200 as shown in FIG. 4. However, as described further herein, a sheath 432 (see FIG. 4, for example) may be included in such embodiments, as the sheath 432 may operably engage the sample container receptacle 1110 so as to urge the sample container receptacle 1110 downward and into the sensor device aperture 1020.

Furthermore, in some such embodiments (as shown generally in FIG. 4) the robotic device (comprising the second robotic device 430, for example) may comprise a fluidics head 435 in fluid communication with the fluidics system 100, wherein the fluidics head 435 is configured for adding a diluent to the sample container 10 and/or removing at least a portion of the preliminary sample from the sample container 10 so as to prepare the sample having the selected concentration of particles.

As shown generally in FIG. 3, in some system 1 embodiments, the robotic system 400 may comprise various components 410, 420, 430 configured to move through a range of motion defined at least in part by an X-axis 401, a Y-axis 402, and a Z-axis 403. According to some such embodiments, the robotic system 400 may comprise a shuttle device 410 (as described herein with respect to FIG. 10, for example) configured for moving the rack 50 along the X-axis 401. As described herein, the shuttle device 410 may comprise, in some embodiments, a linear actuator device configured for movement substantially along a linear axis so as to be capable of advancing the tray 50 along the X-axis 401. In some system 1 embodiments, the shuttle device 410 may advance (and/or "index") the rack 50 to a series of predetermined "stop" positions along the X-axis 401 such that each pair of sample containers 10 and corresponding testing containers 20 may be serviced by the first and second robotic devices 420, 430 (and the fluidics heads 425, 435 and sensor 200 carried thereby) in a substantially linear fashion until all the containers 10, 20 carried by the rack 50 have been processed to produce a series of samples having a selected concentration of particles suspended therein and/or a selected volume that may be compatible, for example, with one or more downstream ID/AST processes (such as, for example, the PHOENIX™ ID/AST system produced by the assignee of the present application). Furthermore, and as described herein, the shuttle device 410 may define one or more register devices for centering and/or operably engaging the rack 50 on the shuttle device 410. For example, the shuttle device 410 may define one or more channels or indentations for receiving a corresponding surface of the rack 50. In other embodiments, the shuttle device 410 may comprise one or more posts or brackets configured to receive a corresponding corner or side wall of the rack 50 such that the shuttle device 410 may effectively position and/or index the rack 50 relative to various components of the system 1. As shown in FIG. 10, the shuttle device 410 may also comprise one or more drive belts 1030 configured for carrying the rack 50 along the X-axis 401 of the system 1 to one or more positions relative to a first robotic device 420 and/or a second robotic device 430 as described further herein. The shuttle device 410 may also comprise one or more conveyors 1040 configured for advancing the rack 50 in an entrance and/or exit queue along the Y-axis 402, for example.

In some embodiments, the shuttle device 410 (and/or an exit queue conveyor thereof, for example) may be operably engaged with an interface 1310 (such as a "pouring station" as shown generally in FIG. 13). The interface 1310 may be configured for receiving the rack 50 so as to facilitate the transfer of the processed sample having the selected concentration of particles to an identification and anti-microbial susceptibility testing (ID/AST) system configured for analyzing the sample so as to identify at least one bacterial component of the sample and/or determine a susceptibility of the at least one bacterial component to an anti-microbial compound. For example, the interface 1310 may be operably engaged with an output queue of the robotic system 400 so as to be capable of receiving a rack 50 containing a plurality of sample containers 10 and a corresponding plurality of testing containers 20.

In some embodiments, the interface 1320 may comprise a substantially "stand-alone" organization station configured for aligning each of a pair of sample containers 10 and testing containers 20 with a corresponding ID/AST disposable that may be placed face-down in one or more registers 1320 configured to receive a corresponding one or more ID/AST disposables (such as, for example, a PHOENIX™ ID/AST disposable manufactured by the assignees of the present application). As shown generally in FIG. 13, the registers 1320 defined in the interface 1310 may be in fluid communication with one or more pouring apertures configured for receiving the processed samples from the sample containers 10 and testing containers 20 disposed in the rack 50. The interface 1310 may thus provide a convenient organizing station where a user may easily view and/or verify the unique indicator 1150 that may be operably engaged with a rotatable status wheel 1120 that may be further operably engaged with the rack 50. As described herein, the unique indicator 1150 may selectively indicate a particular selected concentration of particles of the prepared sample contained in one of the sample container 10 and the testing container 20 (as measured, for example, by the sensor device 200 when the rack 50 is advanced to an analysis position (as shown generally in FIG. 12)). Thus, the interface 1310 may allow a user to quickly view and/or evaluate the unique indicator 1150 (either visually or using a bar code scanner, for example) to ensure that the prepared sample contained in one of the sample container 10 and the testing container 20 includes the selected concentration of particles that is substantially compatible with the ID/AST disposable before applying the prepared sample to the corresponding ID/AST disposable contained, for example, in one or more of the registers 1320. As shown in FIG. 13, the pouring station 1310 may also comprise an inclined portion 1330 configured for orienting the registers 1320 (and therefore, any ID/AST disposables held therein) at an optimal angle such that the prepared samples poured from the sample container 10 and/or the testing container 20 may advance completely through various fluidic pathways that may be defined in an ID/AST disposable to reach one or more microwells containing dried substrates for bacterial ID and/or growth and fluorescent controls.

Furthermore, some system embodiments of the present invention may also comprise an identification and anti-microbial susceptibility testing (ID/AST) system configured for receiving the sample having the selected concentration of particles. For example, the system 1 may comprise an integrated ID/AST system (such as the PHOENIX™ ID/AST system produced by the assignees of the present application) that is configured to receive, for example, one or more ID/AST disposables that may be exposed to one or more of the samples produced according to the process shown schematically in FIGS. 8 and 9 using, for example, the system 1 shown generally in FIG. 3. As described herein, such ID/AST systems may be further configured for identifying at least one bacterial component of the sample (i.e. an "ID" determination) and/or determining a susceptibility of the at least one bacterial component within the sample to an anti-microbial compound (i.e. an "AST" process). The ability of the various system 1 embodiments of the present invention to prepare a sample having a precise concentration of particles (corresponding to a particular optimal bacterial density, for example) may be especially helpful in generating usable AST results. The ID/AST system may comprise, for example, a PHOENIX™ ID/AST system disclosed generally in U.S. Pat. No. 6,096,272, which is hereby incorporated by reference herein in its entirety.

In some system 1 embodiments (as shown generally in FIG. 5), the robotic system 400 may also comprise a first robotic device 420 comprising a first fluidics head 425 in fluid communication with the fluidics system 100. The first robotic device 420 may be configured for moving along at least one of the Y-axis 402 and the Z-axis 403 (so as to be capable of raising and/or lowering the first fluidics head 425 relative to at least one of the sample container 10 and the testing container 20). Thus, using the first fluidics head 425 (which may comprise an automated pipettor) the first robotic device 420 may be capable of adding the diluent to the sample container 10 and/or removing at least a portion of the preliminary sample from the sample container 10 (via aspiration, for example) as the shuttle device 410 moves the rack 50 to a filling position along the X-axis 401 (substantially adjacent to the Y-axis 402 travel of the first robotic device 420, for example). In some system 1 embodiments, the first robotic device 420 may comprise one or more linear actuator configured for advancing and/or retracting one or more fluidics heads 425 along the Y-axis. For example, in some embodiments, the first robotic device 420 may comprise one or more "ZY robots" configured for movement independently along the Y-axis 402 and the Z-axis 403. In such embodiments, as shown generally in FIG. 5, for example, the ZY robots of the first robotic device 420 may be capable of positioning the first fluidics head 425 above at least one of: the ID and testing containers 10, 20 held in the rack 50; a dispensing tip station 500; and a waste container 650 (configured for receiving excess diluent and/or sample material aspirated from one or more containers 10, 20 using the first fluidics head 425). According to some such embodiments, the system 1 may further comprise a dispensing tip station 500 comprising a plurality of disposable dispensing tips 510. In some such embodiments, the robotic system 400 (and more particularly, the first robotic device 420) may be configured for automatically replacing a dispensing tip 510 operably engaged with the fluidics system 100 (and/or with a first fluidics head 425 carried by the first robotic device 420) with at least one of the plurality of disposable dispensing tips 510 after preparing the sample having the selected turbidity level and the selected volume. In other system 1 embodiments, the robotic system 400 may be configured for automatically replacing a dispensing tip 510 operably engaged with the fluidics system 100 with at least one of the plurality of disposable dispensing tips 510 after transferring at least a portion of the sample from the sample container 10 to the testing container 20 and mixing the indicator substance with the sample. Thus, the first robotic device 420 may be capable of utilizing a new disposable dispensing tip 510 for the various dispense and aspirate cycles used to process the sample having the selected turbidity level and selected volume for each new sample container 10 (and corresponding testing container 20) as the shuttle device 410 indexes the tray 50 along the X-axis 401 of the system 1.

In some additional system 1 embodiments, the robotic system 400 may further comprise a second robotic device 430 configured for carrying the sensor 200 along the Z-axis 403 (i.e. for raising and lowering the sensor device 200 relative to the sample container 10 (see FIGS. 4 and 7, for example) so as to position the sensor device 200 adjacent to the sample container 10 along the Z-axis 403. Thus, the second robotic device 430 may be configured for optimally positioning the sensor device 200 for measuring a turbidity level of the preliminary sample in the sample container 10 as the shuttle device 410 moves the rack 50 to an analysis position along the X-axis 401. In some system 1 embodiments, as shown generally in FIG. 4, the rack 50 may further define a channel 55 about the ID aperture 51 that may be sized and configured to receive a complementary sheath 432 that is operably engaged with the second robotic device 430. The sheath 432 may be positioned so as to substantially enclose the sensor device 200 (and/or a scanning head thereof) such that when the second robotic device 430 lowers the sensor device 200 along the Z-axis 403 and into position substantially adjacent to the ID tube 10, the sheath 432 is configured to entering the channel 55 defined in the tray 50 so as to provide a substantially light tight environment about the sample container 10 and the sensor device 200. Thus, the sheath 432 may be configured to shield the sensor device 200 from ambient light present in the environment where the system 1 is operating such that the sensor device 200 is better capable of providing more accurate turbidity readings of the sample disposed in the sample container 10.

As shown in FIGS. 4 and 7, the second robotic device 430 may also comprise a second fluidics head 435 in fluid communication with the fluidics system 100. In some system 1 embodiments, the second fluidics head 435 may comprise an automated pipettor device (as described herein with respect to other components of the fluidics system 100 and the first fluidics head 425). The second fluidics head 435 may be configured for adding a diluent to the sample container 10 (in a dispense cycle) and/or removing at least a portion of the preliminary sample from the sample container 10 (in an aspirate cycle, for example) so as to prepare the sample having the selected concentration of particles. As described herein with respect to other system 1 embodiments, the second fluidics head 435 may also be capable of mixing the sample in the sample container 10 by performing one or more aspirate and dispense cycles (see, for example, the "mix and verify target density achieved" (McF) step shown as step 808 of FIG. 8).

As shown in FIG. 6, the second robotic device 430 may comprise a robotic arm configured for moving about a central axis to a selected angular position Θ relative to the central axis of the robotic arm. Thus, in embodiments wherein the second robotic device 430 comprises a second fluidics head 435 the second robotic device 430 may be configured to be capable of moving through an angle Θ and/or moving along the Z-axis 403 to obtain a supply of diluent from a diluent reservoir (containing, for example, a supply of sterile saline solution) and swing through the angle Θ to a position adjacent to the sample container 10 so as to be capable of dispensing the diluent into the sample container 10. Furthermore, in some embodiments, as shown in FIG. 6, the system 1 may further comprise a wash station 600 configured for receiving the sensor device 200 and the second fluidics head 435 when the second robotic device 430 is not in use. The wash station 600 may be further configured for washing at least one of the sensor 200 and the second fluidics head 435 between dispensing, aspirating, and/or measuring cycles when the second robotic device 430 is "parked" in the wash station 600.

As shown in FIG. 3, some system 1 embodiments may further comprise a user interface 700 integrated with and/or in communication with the controller device 300. The user interface 700 may be configured for receiving a user input comprising at least one of the selected concentration of particles and/or the selected volume of the sample. According to various system 1 embodiments, the user interface 700 may comprise a display (such as a touch-screen LCD, for example) and/or other user interface components including, but not limited to: a keyboard/keypad; a mouse/trackball; and alarm elements (such as speakers and/or indicator lights). The user interface 700 may thus also be configured for allowing a user to monitor and/or control the operation of the system 1. For example, the user interface 700 may provide visual and/or auditory feedback to a user regarding system 1 status. Such feedback may include, but is not limited to: diluent-level sensing; alarms; disposable dispensing tip 510 inventory status; tray 50 position status; sample container 10 and/or testing container 20 inventory; and other system 1 monitoring feedback.

As shown generally in FIGS. 8-9, various embodiments of the present invention may also provide methods for automatically preparing a sample having a selected concentration of particles (expressed, in some embodiments, as a turbidity level, for example) and/or a selected volume in a sample container 10 containing a preliminary sample. As shown generally in FIG. 9 the method may first comprise step 805 for measuring a concentration of particles suspended in the preliminary sample using a sensor device 200. The method further comprises step 806 for determining an overall dilution scheme that may comprise, for example, an amount of diluent to be added to the sample container 10 to prepare a sample having the selected concentration of particles, and/or an amount of the preliminary sample to be removed from the sample container 10 prior to adding diluent, to avoid any overflow from the sample container 10, using a controller device 300 in communication with the sensor device 200. In addition, the method further comprises step 807 for adding the determined amount of diluent and/or removing the determined amount of preliminary sample determined in step 806 using an automated fluidics system 100 in communication with the controller device 300, so as to prepare a sample having the selected concentration of particles suspended therein. Finally, in some embodiments, the method further comprises step 810 for removing at least a portion of the sample from the sample container 10 using the automated fluidics system 100, such that the sample container 10 contains the sample having the selected volume. It should be understood that the methods shown, for example, in FIGS. 8 and 9 may be performed by a substantially automated system.

FIG. 8 shows another exemplary embodiment of the methods of the present invention including additional method steps that may be performed in order to prepare a sample having a selected concentration of particles and/or a selected volume in a sample container 10 containing a preliminary sample. It should be understood that the steps depicted generally in FIG. 8 (especially the selected concentration of particles (shown in terms of a turbidity measured against the McFarland (McF) scale)) steps 806-806*a* as well as step 807, are specific to exemplary samples having selected turbidity levels of either 0.25 McF or 0.5 McF, respectively which may outline selected particle concentrations that are suitable for use in downstream ID/AST processes such as those performed by the PHOENIX™ ID/AST system produced by the assignees of the present application (which may be set to utilize samples having a density of either 0.25 McF or 0.5 McF depending at least in part on the type of bacteria or other particles that are targeted for identification and/or testing to determine antimicrobial susceptibility). It should be further understood that various method embodiments of the present invention may be used to prepare samples having a variety of selected concentrations of particles and/or volumes other that those exemplary values shown in FIG. 8.

As shown in FIG. 8, various method embodiments may further comprise step 801 for loading consumables into a system 1 such as that system described generally herein with respect to FIG. 1. The consumables may include, but are not limited to: disposable dispensing tips 510; diluent (such as bulk sterile saline solution, for example); and indicator substance (such as bulk AST indicator substance that may be dispensed into a testing container 20 as part of step 812, for example). The method may further comprise step 802 for loading a rack 50 with a preliminary sample (contained, for example, in a sample container 10, such as an ID tube). Once the consumables and sample rack 50 are loaded, the process may be initiated (see, for example, element 800 denoting the process start). The method may further comprise, in some embodiments, step 800a for checking an inventory and/or status of the consumables (such as AST reagent, or other consumables) before entering into the subsequent steps for preparing a sample having a selected concentration of particles and/or volume. As described herein with respect to various system 1 embodiments of the present invention, step 800a may be performed by the controller device 300 and results generated by step 800a may be presented to a user in a status report and/or status indicator communicated via a user interface 700 (such as a display and/or alarm indicator). Furthermore, if one or more reagents or other consumables are not detected onboard the system, the controller device 300, in some embodiments, may automatically suspend the method shown in FIG. 8 (see, for example, element 800b).

Furthermore, some method embodiments may further comprise step 804 for mixing the preliminary sample contained in the sample container 10 prior to performing step 805 for measuring a concentration of particles suspended in the preliminary sample (i.e. "reading" a density of the sample using a nephelometer or other sensor device 200). As shown in FIG. 8, step 804 may, in some embodiments, further comprise detecting a level of the preliminary sample in the sample container (using, for example, a sensor tip (i.e. a capacitive tip) in communication with the controller 300). Level detection in step 804 may be accomplished, for example, by lowering one or more sensor tips into the sample container 10 using one or more fluidics heads 425 carried by a robotic device (such as one or more replicates of the first robotic device 420 shown generally in FIGS. 3 and 5). Step 804 may further comprise storing the detected level of the preliminary sample (using, for example, a memory device integrated with the controller device 300) for comparison with a sample container 10 fluid level obtained later in step 810. As described herein with respect to various system 1 embodiments, any mixing step (such as step 804) may be performed by an automated fluidics system 100 (such as a pipettor) in a series of aspirate and/or dispense cycles.

As shown herein with respect to FIG. 8, the method may further comprise step 805 for measuring a concentration of particles suspended in the preliminary sample (using a sensor device 200, such as a nephelometer, for example). Furthermore, based at least in part on the measured concentration of particles (expressed as a turbidity level in some embodiments), the controller device 300 described herein may be further configured to perform step 806 for determining an overall dilution scheme (i.e. an amount of diluent to be added to the sample container 10 and/or an amount of the preliminary sample to be removed from the sample container 10) for preparing a sample having a selected concentration of particles suspended therein (and that will not overfill and/or underfill a sample container 10 having a known volume).

Thus, as shown in FIG. 8, step 806 may comprise various subroutines and/or decision points for determining quantities of an overall dilution scheme, which may comprise an amount of diluent to be added to the sample container 10 and/or an amount of the preliminary sample to be removed from the sample container 10 to arrive at a sample having a selected concentration of particles suspended therein (given a measured concentration of particles suspended in the preliminary sample measured in step 805). For example, in embodiments wherein the concentration of particles is expressed as a turbidity measurement, step 806a may comprise determining if the turbidity level (i.e. "density" in McF, for example) is initially too low (i.e. below a minimum turbidity relative to 0.25 and 0.5 McF targets, for example). If step 806a results in a positive result (i.e. density too low), then the process may be halted (i.e. the sample container 10 may be rejected). If the density (turbidity or measured concentration of particles determined in step 805) is sufficient to allow for the application of the determined dilution scheme (see step 806), then the method may progress to step 807 as discussed further herein.

As shown generally in FIG. 8, step 807 generally comprises adding the determined amount of diluent to the sample container 10 or removing the determined amount of the preliminary sample from the sample container 10 prior to adding diluent to prevent, for example, overflow of the sample container 10 (using an automated fluidics system 100, for example) in communication with the controller device 300, so as to prepare a sample having the selected concentration of particles (i.e. a sample that complies substantially with the dilution scheme determined in step 806). Depending on the detected concentration of particles determined in step 805 (and the corresponding dilution scheme determined in step 806), the method may comprise adding diluent to the sample container 10 (such as bulk saline) and/or removing at least a portion of the overall preliminary sample from the sample container 10 (which may contain both diluent and a portion of the sample particles suspended therein) in order to achieve a selected target level of dilution (which may correspond to the selected concentration of particles in the sample). As described herein, in some embodiments, a user may select one or more target particle densities that may be optimal for certain types of ID and/or AST processes. For example, in some embodiments the selected concentration of particles may include, but is not limited to 0.25 McF and 0.5 McF. As shown in FIG. 8, step 807 may further comprise aspirating fluid from the sample container 10 (which may include diluent as well as sample particles suspended therein) in order to "reset" the level of the prepared sample to the volume detected originally in step 804.

Step 808 may comprise mixing the sample having the selected concentration of particles suspended therein prior to removing at least a portion of the sample from the sample container using the automated fluidics system. Step 808 may be performed via one or more aspirate/dispense cycles using the second fluidic head 435 (carried, for example, by a second robotic device 430). As shown in FIG. 7, because step 808 may be performed by a second robotic device 430 carrying both the second fluidic head 435 and the sensor device 200, step 808 may also comprise verifying the concentration of particles suspended therein (using the sensor device 200) of the sample prior to removing at least a portion of the sample from the sample container 10 using the automated fluidics system 100.

As shown generally in step 809, the controller 300 (and/or a user performing the method embodiments described herein) may read the verified concentration of particles determined in step 808 and either reject the tube (if the measured concentration of particles from step 808 is not substantially equivalent to the selected concentration of particles) or proceed with the downstream method steps 810-816. Some method embodiments may further comprise step 810 for verifying the fluid level (i.e. a level of the preliminary sample) in the sample container 10 using a second sensor tip (i.e. a disposable capacitive tip carried by one or more fluidics heads 425 operably engaged with a robotic device 420). As described herein, the robotic system 400 may comprise, in some embodiment, a pair dedicated robotic devices 420 wherein one of the robotic devices is tasked with performing the steps 808 and 809 (i.e. performing the dispense and/or aspiration steps mandated by the dilution scheme determined in step 806) and the other robotic device is responsible for transferring a portion of the prepared sample to a corresponding testing container 20 for AST sample preparation (see steps 811-814). Thus, the second "AST" preparation robotic device 420 may comprise a separate fluidics head 425 carrying a second sensor tip configured for independently verifying the level of the prepared sample in the sample container 10 prior to transferring at least a portion of the prepared sample to the corresponding testing container 20.

FIG. 8 also shows an additional method step 811 for determining if a testing container 20 is present that may correspond to a given sample container 10. If not, the method ends at step 811. However, if a testing container 20 is present, the method may proceed to steps 812-814 which comprise steps for preparing a testing container 20 for downstream AST processes, for example, by adding and/or mixing an indicator substance to a portion of the sample having the selected concentration of particles and/or volume. It should be understood that in various method embodiments, steps 812-814 may be performed by one or more components of a fluidics system 100 as part of a complete system 1 as described herein. Step 812 comprises dispensing an indicator substance in the testing container 20 using the automated fluidics system 100 and mixing using the automated fluidics system 100. Step 813 comprises transferring at least a portion of the sample having the selected concentration of particles and/or the selected volume to a testing container 20 corresponding to the sample container 10 using the automated fluidics system 100 and mixing the at least a portion of the sample and the indicator substance in the testing container 20 using the automated fluidics system 100. As described herein with respect to several system 1 embodiments, the various mixing steps performed, for example, as part of steps 812 and 813 may be performed by an automated fluidics system 100 comprising an automated pipettor configured to repeatedly aspirate from and/or dispense to the testing container 20 in order to achieve the desired level of mixing. Furthermore, step 814 comprises updating a rack status indicator (see, for example, the rotatable status wheel 1120 shown in FIG. 11. As described herein with respect to FIG. 11, the step 814 may be performed by a rotating actuator 1127 configured for selectively engaging a stem 1125 of the status wheel 1120 when the rack 50 is at a particular position within the system 1 (such as an analysis position with respect to the sensor device 200 (as shown generally in FIG. 12)). The rotating actuator 1127 may be in communication with the sensor device 200 (via the controller device 300, for example) such that the rotating actuator 1127 may be responsive to the concentration of particles (expressed in some embodiments as a turbidity) determined by the sensor device 200. Therefore, in some embodiments, the rotating actuator 1127 may be configured for rotating the status wheel 1120 relative to the rack 50 such that the unique indicator 1150 that is visible via the status window 1130 defined in the rack 50 substantially corresponds to the selected concentration of particles (expressed, for example, as turbidity on the McFarland Scale) in the prepared sample.

As shown in FIG. 8, various method embodiments may also comprise step 815 for determining if additional sample containers 10 are present in the system 1. If so, the method may return to step 807 such that the dilution scheme determined in step 806 may now be applied to another sample container 10 (which may be indexed forward in some method embodiments by a shuttle device 410 configured for systematically advancing a rack 50 containing the sample containers 10 along an axis of the system 1). If no additional sample containers 10 are detected in step 815, the method may proceed to step 816 for removing a completed rack 50 of sample containers 10 and corresponding testing containers 20 for use in a downstream process requiring samples having a selected concentration of particles (such as a selected bacterial density required for downstream microdilution ID/AST tests, for example).

In addition to providing systems and methods, the present invention also provides computer program products for performing the various steps and combinations of steps described above. The computer program products may operate via a computer-readable storage medium having computer readable program code embodied in the medium. With reference to FIG. 1, the computer readable storage medium may be part of the controller device 300, and may implement the computer readable program code to perform the above discussed steps.

In this regard, FIGS. 8-9 are block diagram, flowchart and control flow illustrations of methods, systems 1 and computer program products according to exemplary embodiments of the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus (including, for example, the controller device 300 described herein) to produce a machine, such that the instructions which execute on the computer or other programmable apparatus are capable of implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instructions which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of steps for performing the specified functions, and program instructions for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for automatically preparing a sample having a selected concentration of particles therein and a selected volume in a sample container containing a preliminary sample, the method comprising:

measuring a concentration of particles in the preliminary sample using a sensor device;

determining at least one of an amount of diluent to be added to the sample container and an amount of the preliminary sample to be removed from the sample container, to prepare the sample having the selected concentration of particles and the selected volume, using a controller device in communication with the sensor device; and adding the determined amount of diluent to the sample container or removing the determined amount of the preliminary sample from the sample container, using an automated fluidics system in communication with the controller device, so as to prepare the sample having the selected concentration of particles and the selected volume.

2. A method according to claim 1, further comprising removing at least a portion of the sample from the sample container using the automated fluidics system, such that the sample container contains the sample having the selected volume.

3. A method according to claim 1, wherein the determining step comprises:

determining if the sample having the selected concentration of particles may be prepared by adding the determined amount of diluent without exceeding a maximum volume of the sample container; and determining if the sample having the selected concentration of particles may be prepared by adding the determined amount of diluent to prepare a sample having at least a minimum volume.

4. A method according to claim 1, further comprising transferring at least a portion of the sample having the selected concentration of particles and the selected volume to a testing container corresponding to the sample container using the automated fluidics system.

5. A method according to claim 4, further comprising:

dispensing an indicator substance in the testing container using the automated fluidics system; and mixing the at least a portion of the sample and the indicator substance in the testing container using the automated fluidics system.

6. A method according to claim 1, further comprising mixing the preliminary sample using the automated fluidics system before determining the concentration of particles in the preliminary sample.

7. A method according to claim 1, further comprising mixing the sample having the selected concentration of particles using the automated fluidics system prior to removing at least a portion of the sample from the sample container.

8. A method according to claim 1, wherein the automated fluidics system further comprises a dispensing tip station comprising a plurality of disposable dispensing tips, the method further comprising replacing a dispensing tip operably engaged with the automated fluidics system with at least one of the plurality of disposable dispensing tips after removing at least a portion of the sample from the sample container.

9. A method according to claim 1, further comprising washing the sensor device using a wash station configured for receiving the sensor device.

10. A method according to claim 1, further comprising receiving a user input comprising at least one of the selected concentration of particles and the selected volume of the sample via a user interface in communication with the controller device.

* * * * *